(12) United States Patent
Treco et al.

(10) Patent No.: US 7,229,793 B1
(45) Date of Patent: Jun. 12, 2007

(54) CONSTRUCTS AND CELLS FOR PRODUCTION OF SMALL PEPTIDES

(75) Inventors: Douglas A. Treco, Arlington, MA (US); Michael F. Concino, Bolton, MA (US); Stephen J. Duguay, Salem, MA (US)

(73) Assignee: Shire Human Genetic Therapies, Inc., Cambridge, MA (US)

( * ) Notice: Subject to any disclaimer, the term of this patent is extended or adjusted under 35 U.S.C. 154(b) by 379 days.

(21) Appl. No.: 09/716,166

(22) Filed: Nov. 17, 2000

Related U.S. Application Data

(60) Provisional application No. 60/166,508, filed on Nov. 19, 1999.

(51) Int. Cl.
| | |
|---|---|
| C12N 15/09 | (2006.01) |
| C12N 15/00 | (2006.01) |
| C12N 5/00 | (2006.01) |
| A61K 38/26 | (2006.01) |

(52) U.S. Cl. .................. 435/69.4; 435/320.1; 435/325; 530/308

(58) Field of Classification Search .............. 435/69.4, 435/320.1, 252.3, 325; 530/308
See application file for complete search history.

(56) References Cited

U.S. PATENT DOCUMENTS

| | | | | |
|---|---|---|---|---|
| 5,118,666 | A * | 6/1992 | Habener | |
| 5,641,670 | A * | 6/1997 | Treco et al. ................ | 435/325 |
| 5,891,671 | A * | 4/1999 | Suzuki et al. | |
| 6,010,883 | A * | 1/2000 | Nagai et al. ............... | 435/69.7 |
| 6,531,124 | B1 * | 3/2003 | Selden et al. ........... | 424/93.21 |

FOREIGN PATENT DOCUMENTS

| | | |
|---|---|---|
| EP | 0 157 753 B1 | 11/1987 |
| EP | 0 770 995 A2 | 3/1996 |
| EP | 0 775 750 A2 | 5/1997 |
| WO | WO 92/10576 | 6/1992 |
| WO | WO 93/09222 | 5/1993 |
| WO | WO 97/29180 | 8/1997 |
| WO | WO 98/37910 | 9/1998 |
| WO | WO 99/29336 | 6/1999 |

OTHER PUBLICATIONS

Patel et al. Processing and intracellular targeting of prosomatostatin-derived peptides: the role of mammalian endoproteases. 1995, CIBA Foundation Sumposium, 190: 26-50.*

Gerich et al. Prolonged intravenous and subcutaneous somatostatin in treatment of human diabetes. 1976, Diabetes, 25 (suppl. 1): 340.*

Warren et al. Expression of preprosomatostatin in heterologous cells: biosynthesis, posttranslational processing, and secretion of mature somatatin, Cell, 1984, 39(3 Pt2): 547-55.*

Schwartz, "The Processing of Peptide Precursors Proline-directed Arginyl Cleavage and Other Monobasic Processing Mechanisms", FEBS Letters 200:1-10, 1986, XP-002164412.

Stroller et al., "The Propeptide of Preprosomatostatin Mediates Intracellular Transport and Secretion of α-Globin from Mammalian Cells", Journal of Cell Biology 108:1647-1656, 1989, XP-000990902.

Argos et al., "Nucleotide and Amino Acid . . . ," The Journal of Biological Chemistry, 258(14):8788-8793, 1983.

Chen et al., "The Propeptide of Anglerfish . . . ," The Journal of Biological Chemistry, 270(31)18598-18605, 1995.

Fisher et al., "Multiple Neuropeptides Derived . . . ," Cell, 54:813-822, 1988.

Moore et al., "Secretory Protein Targeting . . . " The Journal of Cell Biology, 101:1773-1781, 1985.

Sevarino et al., "Amino-Terminal Sequences . . . ," Cell, vol. 57:11-19, 1989.

Stoller et al., "The Propeptide of Preprosomatostatin . . . ," The Journal of Cell Biology, 108:1647-1655, 1989.

GenBank Accession No. NP_001039, Jul. 26, 1999.

GenBank Accession No. AAD39138, Jun. 16, 1999.

GenBank Accession No. AAC04697, Apr. 20, 1999.

Stoller & Shields, "The role of paired basic amino acids in mediating proteolytic cleavage of prosomatostatin. Analysis using site-directed mutagenesis", Journal of Biological Chemistry 264: pp. 6922-6928 (1989).

Danoff et al., "Intracellular degradation of prohormone-chloramphenicol-acetyl-transferase chimeras in a pre-lysosomal compartment", Eur. J. Biochem. vol. 218, pp. 1063-1070 (1993).

* cited by examiner

*Primary Examiner*—Gary B. Nickol
*Assistant Examiner*—Dong Jiang
(74) *Attorney, Agent, or Firm*—Fish & Richardson P.C.

(57) ABSTRACT

The present invention features a nucleic acid construct for expressing a product, e.g., a small peptide such as GLP-1. The construct includes a nucleic acid sequence encoding a signal peptide and a nucleic acid sequence which encodes the pro-region of somatostatin or a functional fragment thereof. The construct can further include a sequence encoding the small peptide or the construct can be used to express an endogenous genomic sequence encoding the small peptide. The present invention further features genetically engineered cells, and methods of using such constructs or cells.

41 Claims, 5 Drawing Sheets

FIG. 3

```
BamHI
GGA TCC atg ctg tcc cgc tgc tgc cag cte gct gcg ctg tce atc
         gtc ctg ctg gcc aag gtc tgt gtc acc ggc ccc gac aga ctc cgt
cag ttt ctg cag ttg gca tcc gag gct ctg tct cag acg gat gcc
aag tac ttc tte gca gaa gat gct ctg tee cag ccc gag cag atg aat
gcc ctg gaa cct gaa cga CGC GCA CGA GCT CGG AGA CAT GCT GAA GGG GAA ACC TTT ATT
gtc ctg atg ctg CGC GCA CGA GCT CGG AGA CAT GCT GAA GGG GAA ACC TTT ATT
AGT GAT GTA AGT TCT TAT TTG GAA GGC CAA GCT GCC AAG GAA TTC ATT GCT
TGG CTG GTG AAA GGC CGA CGA TAA CTC GAG
                                     *   XhoI
```

FIG. 4

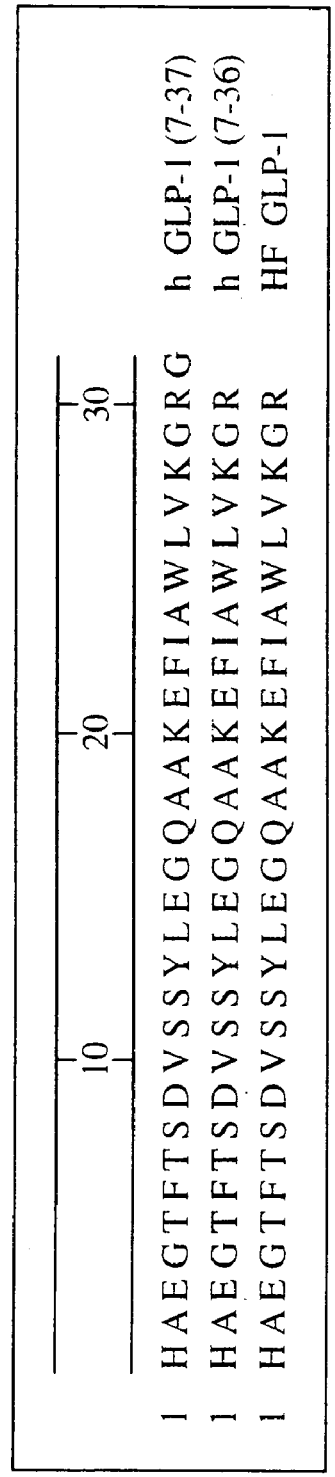

```
1  HAEGTFTSDVSSYLEGQAAKEFIAWLVKGRG    h GLP-1 (7-37)
1  HAEGTFTSDVSSYLEGQAAKEFIAWLVKGR     h GLP-1 (7-36)
1  HAEGTFTSDVSSYLEGQAAKEFIAWLVKGR     HF GLP-1
```

CONSTRUCTS AND CELLS FOR PRODUCTION OF SMALL PEPTIDES

This application claims the benefit of a previously filed Provisional Application No. 60/166,508, filed Nov. 19, 1999, the contents of which is incorporated in its entirety.

BACKGROUND OF THE INVENTION

Gene products, e.g., neuropeptides and small peptide hormones, are often synthesized as part of a larger inactive polyprotein precursor. To generate a bioactive or processed molecule, a precursor can undergo one or several posttranslational modifications. These modifications can include glycosylation, cleavage, phosphorylation, amidation, and acetylation. The processing events can occur in different organelles during intracellular transport. Peptides can then be sorted in secretory granules until an extracellular signal triggers secretion. In order for the peptide to be secreted in active form, the peptide has to be properly processed in the cell including cleavage of the precursor sequences.

SUMMARY OF THE INVENTION

The present invention is based, in part, on the discovery that fusion to a signal sequence and a functional pro-region of somatostatin can optimize the production, e.g., one or more of the synthesis, processing or secretion, of a small heterologous peptide in a cell, or a heterologous protein in a cell in which somatostatin is not normally expressed. It was found that a product, such as GLP-1, can be obtained in active form from a cell, e.g., a primary cell, a secondary cell or a cell line, when the nucleic acid sequence encoding GLP-1 is expressed as part of a construct which also includes a nucleic acid sequence encoding prepro-somatostatin or functional fragments or variants thereof. In addition, it was discovered that a product, such as GLP-1, can be obtained from a cell such that the product obtained includes a pro-somatostatin region. Such products can be used, for example, to decrease degradation of the product in vitro or in vivo.

Accordingly, in one aspect, the invention features, a nucleic acid construct for expression of a small peptide. The construct includes: a nucleic acid sequence encoding a signal peptide; a nucleic acid sequence which encodes the pro-region of a somatostatin or a functional fragment or variant thereof; and a nucleic acid sequence encoding a small peptide.

In a preferred embodiment, the nucleic acid sequence encoding the signal peptide is from the pre-region of a somatostatin.

In a preferred embodiment, the nucleic acid sequence encoding the small peptide is a cDNA or a genomic sequence.

In a preferred embodiment, the small peptide is: a small hormone; an anti-diabetogenic peptide; an anti-diabetogenic peptide selected from the group consisting of glucagons-like peptide (GLP-1), e.g., GLP-1 (7-37), GLP-1 (7-36), insulin, insulin-like growth factor-1, insulin-like growth factor-2, exendin-4, gastric inhibitory polypeptide and analogs thereof. In a preferred embodiment, the analog of GLP-1 is GLP-1 Gly8.

In a preferred embodiment, the small peptide is produced in mature form, e.g., the pro-region of somatostatin is cleaved from the small peptide. In a preferred embodiment, there is a site between the pro-region and the sequence encoding the small peptide at which the small peptide can be cleaved from a precursor. The site can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, the site is: part of the pro-region of a somatostatin nucleic acid sequence; part of the nucleic acid sequence of the small peptide; formed at the junction of the pro-region and the sequence encoding the small peptide; a nucleic acid sequence encoding at least 1, 2, 3, 4, 5, 6, 8, 10 amino acid residues but preferably not more than 30 to 50 amino acid residues. In a preferred embodiment, the nucleic acid sequence encodes a multibasic cleavage site having the amino acid sequence Arg-Ala-Arg-Ala-Arg-Arg (SEQ ID NO:1). In another preferred embodiment, the nucleic acid sequence encodes a cleavage site having the amino acid sequence X-Arg-X-X-Arg. In a preferred embodiment, the site is cleaved such that the small peptide does not include any extraneous sequence. In another preferred embodiment, the site is cleaved such that the small peptide includes less than 10, 5, 4, 3, 2, or 1 extraneous amino acid residues.

In another preferred embodiment, the small peptide is produced as a fusion peptide, e.g., a fusion peptide which includes a pro-region of somatostatin or a functional fragment thereof and a small peptide.

In a preferred embodiment, when the small peptide is produced as a fusion peptide, there is a site between the pro-region and the sequence encoding the small peptide. The site can be a nucleic acid encoding at least 1, 2, 3, 4, 5, 6, 8, 10 amino acids but preferably not more than 30 to 50 amino acids. In a preferred embodiment, the site can be: a nucleic acid sequence encoding amino acids which are not cleaved, e.g., the site is not recognized by an enzyme capable of cleaving the site; a nucleic acid encoding a site capable of being cleaved, e.g., a site which is recognized and cleaved by an enzyme; a nucleic acid encoding an altered site which is recognized and cleaved by an enzyme but is cleaved less efficiently than the site normally recognized by the enzyme.

In a preferred embodiment, when the small peptide is produced as a fusion peptide having a site which is not capable of being cleaved, the site includes at least 1, 2, 3, 4, 5, 6, 8, 10 amino acids but preferably not more than 30 to 50 amino acids which are not recognized as a cleavage site by an enzyme, e.g., an endoprotease. For example, a site which is not capable of being cleaved can be a series of alanine residues, e.g., at least 1, 2, 3, 4, 5, 6, 8, or 10 alanine residues.

In a preferred embodiment, when the small peptide is produced as a fusion peptide having a site which is capable of being cleaved, the site can include at least 1, 2, 3, 4, 5, 6, 8, 10 but preferably not more than 30 to 50 amino acids which are recognized as a cleavage site by an enzyme. A site capable of being cleaved can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, an enzyme which is preferentially expressed in a tissue or fluid recognizes the site capable of being cleaved. For example, the enzyme can be an enzyme preferentially expressed in blood. An example of a site recognized by an enzyme preferentially expressed in blood is a blood coagulation cleavage site, e.g., a blood coagulation factor Xa cleavage site, e.g., a site having the amino acid sequence $X_1$-$X_2$-Gly-Arg, wherein $X_1$ is Iso, Leu, Pro or Ala and $X_2$ is a Gly, Asp, Gln or Asn residue. Other blood coagulation cleavage sites are described, for example, in U.S. Pat. No. 6,010,883, the contents of which is incorporated herein by reference.

In preferred embodiment, when the small peptide is produced as a fusion peptide, the fusion peptide includes an altered site which is recognized and cleaved by an enzyme but is cleaved less efficiently than the site normally recognized by the enzyme. For example, the site can be a cleavage site which is recognized by an enzyme, e.g., an endoprotease, but which has been modified such that the enzyme cleaves the site less efficiently than the unmodified cleavage site. The site can be modified such that at least 1, 2, 3, 4, 5, 6, 8, or 10 amino acids are substituted, deleted or added to the cleavage site. For example, a site having 1, 2, or 3 arginine(s) is less efficiently recognized by the endoprotease furin than a site having 4 or more arginine residues.

In a preferred embodiment, when the small peptide is produced as a fusion peptide having a site capable of cleavage (e.g., a site which is cleaved by an enzyme or an altered site which is recognized by an enzyme but cleaved less efficiently than an unaltered site), the site is: part of the pro-region of a somatostatin nucleic acid sequence; part of the nucleic acid sequence of the small peptide; formed at the junction of the pro-region and the sequence encoding the small peptide; the site is cleaved such that the small peptide does not include any extraneous sequence; the site is cleaved such that the small peptide includes less than 10, 5, 4, 3, 2, or 1 extraneous amino acid residues.

In another preferred embodiment, the small peptide is produced as a fusion peptide and there are no additional amino acids present between the pro-region and the small peptide.

In a preferred embodiment, the construct further includes at least one regulatory sequence. In a preferred embodiment, the regulatory sequence is a 5' regulatory sequence, e.g., a 5' flanking sequence (e.g., a promoter and/or an enhancer), and/or 5' untranslated region (5' UTR); a 3' regulatory sequence, e.g., a 3' untranslated region (3' UTR) (e.g., a polyadenylation sequence), a 3' flanking sequence; at least one splice junction. The regulatory sequence can be a viral or a non-viral sequence. In a preferred embodiment, the regulatory sequence can be: the regulatory sequence that normally occurs with the small peptide; the regulatory sequence of CMV, elastase, aldolase, or other constitutively active regulatory sequences; a glucose-responsive regulatory sequence, e.g., an insulin regulatory sequence; a regulatory sequence involved in feeding/satiety behavior, e.g., a leptin regulatory sequence.

In a preferred embodiment, the nucleic acid sequence encodes: the pro-region of human somatostatin or a functional fragment or sequence variant thereof; the pre-region of human somatostatin or a functional fragment thereof; the prepro-region of human somatostatin or a functional fragment or sequence variant thereof. In a preferred embodiment, the pre-, pro-, or prepro-region differs from wild-type by 1 but not more than 5, 10, 12, 25, 27, 30, 35, 40, 44, 48, 50 amino acid residues.

In a preferred embodiment, the small peptide is a small human peptide, e.g., a small human hormone, e.g., a human anti-diabetogenic peptide, e.g., human GLP-1, e.g., GLP-1 (7-37), GLP-1 (7-36), or a fragment or variant thereof. In a preferred embodiment, the nucleic acid sequence encoding a small peptide is a synthetic nucleic acid, e.g., a synthetic nucleic acid which encodes a small peptide wherein at least one non-common or less common codon of the peptide has been replaced by a common codon.

In another aspect, the invention features, a cell which includes an exogenous nucleic acid sequence, e.g., one described herein. The exogenous nucleic acid sequence includes: a nucleic acid sequence encoding a signal peptide; a nucleic acid sequence which encodes the pro-region of a somatostatin or a functional fragment or variant thereof; and a nucleic acid sequence encoding a product, e.g., a small peptide.

In a preferred embodiment, the exogenous nucleic acid sequence is integrated into the genome of the cell. In another preferred embodiment, the exogenous nucleic acid sequence is carried on an extra chromosomal element, e.g., plasmids, episomes, cosmids, phagemids and artificial chromosomes.

In a preferred embodiment, the cell is: a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells; a transformed or immortalized cell line; a cell other than an endocrine cell; one in which somatostatin is not normally expressed. Preferably, the cell is a human cell. Examples of immortalized human cell line useful in the present method include, but are not limited to: a Bowes Melanoma cell (ATCC Accession No. CRL 9607), a Daudi cell (ATCC Accession No. CCL 213), a HeLa cell and a derivative of a HeLa cell (ATCC Accession Nos. CCL2 CCL2.1, and CCL 2.2), a HL-60 cell (ATCC Accession No. CCL 240), a HT1080 cell (ATCC Accession No. CCL 121), a Jurkat cell (ATCC Accession No. TIB 152), a KB carcinoma cell (ATCC Accession No. CCL 17), a K-562 leukemia cell (ATCC Accession No. CCL 243), a MCF-7 breast cancer cell (ATCC Accession No. BTH 22), a MOLT-4 cell (ATCC Accession No. 1582), a Namalwa cell (ATCC Accession No. CRL 1432), a Rafji cell (ATCC Accession No. CCL 86), a RPMI 8226 cell (ATCC Accession No. CCL 155), a U-937 cell (ATCC Accession No. 1593), WI-28VA13 sub line 2R4 cells (ATCC Accession No. CLL 155), a CCRF-CEM cell (ATCC Accession No. CCL 119) and a 2780AD ovarian carcinoma cell (Van Der Blick et al., Cancer Res. 48:5927–5932, 1988), as well as heterohybridoma cells produced by fusion of human cells and cells of another species. In another embodiment, the immortalized cell line can be cell line other than a human cell line, e.g., a CHO cell line, a COS cell line.

In a preferred embodiment, the nucleic acid sequence encoding the product, e.g., can be a cDNA or a genomic sequence.

In a preferred embodiment, the cell further includes at least one regulatory sequence, sufficient for expression of the exogenous nucleic acid sequence in the cell. In a preferred embodiment, the regulatory sequence is a 5' regulatory sequence, e.g., a 5' flanking sequence (e.g., a promoter and/or an enhancer), and/or 5' untranslated region (5'UTR); a 3' regulatory sequence, e.g., a 3' untranslated region (3'UTR) (e.g., a polyadenylation sequence) and/or a 3' flanking sequence; at least one splice junction site. The regulatory sequence can be a viral or non-viral sequence. In a preferred embodiment, the regulatory sequence can be: the regulatory sequence that normally occurs with the product, the regulatory sequence of CMV, elastase, aldolase, or other constitutively active regulatory sequences; a glucose-responsive regulatory sequence, e.g., an insulin regulatory sequence; a regulatory sequence involved in feeding/satiety behavior, e.g., a leptin regulatory sequence.

In a preferred embodiment, the sequence encoding the signal peptide is from the pre-region of a somatostatin.

In a preferred embodiment, the small peptide is: a small hormone; a neuropeptide; an anti-diabetogenic peptide, e.g., an anti-diabetogenic peptide selected from the group consisting of glucagons-like peptide-1 (GLP-1), e.g., GLP-1 (7-37), GLP-1 (7-36), glucagons-like peptide-2 (GLP-02), insulin, insulin-like growth factor-1, insulin-like growth factor-2, exendin-4, gastric inhibitory polypeptide and analog thereof. In a preferred embodiment, the analog of GLP-1 is GLP-1 Gly8.

In a preferred embodiment, the small peptide is normally contained within a secretory vesicle within the cell.

In a preferred embodiment, the product, e.g., small peptide, is produced in mature form, e.g., the pro-region of somatostatin is cleaved from the small peptide. In a preferred embodiment, there is a site between the pro-region and the sequence encoding the small peptide at which the small peptide can be cleaved from a precursor. The site can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4 substilisin-related pro-protein convertase, PC1, PC2, PC6 or PC7. In a preferred embodiment, the site is: part of the pro-region of a somatostatin nucleic acid sequence; part of the nucleic acid sequence of the product formed at the junction of the pro-region and the sequence encoding the product; a nucleic acid sequence encoding at least 1, 2, 3, 4, 5, 6, 8, 10 amino acid residues but preferably not more than 30 to 50 residues. In a preferred embodiment, the nucleic acid sequence encodes a multibasic cleavage site having the amino acid sequence Arg-Ala-Arg-Ala-Arg-Arg (SEQ ID NO:1). In another preferred embodiment, the nucleic acid sequence encodes a cleavage site having the amino acid sequence X-Arg-X-X-Arg. In a preferred embodiment, the site is cleaved such that the product, e.g., small peptide, does not include any extraneous sequence. In another preferred embodiment, the site is cleaved such that the product, e.g., small peptide, includes less than 10, 5, 4, 3, 2, or 1 extraneous amino acid residues.

In another preferred embodiment, the product, e.g., small peptide, is produced as a fusion product, e.g., a fusion peptide which includes a pro-region of somatostatin or a functional fragment thereof and a product, e.g., a small peptide.

In a preferred embodiment, when the product is produced as a fusion peptide, there is a site between the pro-region and the sequence encoding the product, e.g., the small peptide. The site can be a nucleic acid encoding at least 1, 2, 3, 4, 5, 6, 8, 10 amino acids but preferably not more than 30 to 50 amino acids. In a preferred embodiment, the site can be: a nucleic acid sequence encoding amino acids which are not cleaved, e.g., the site is not recognized by an enzyme capable of cleaving the site; a nucleic acid encoding a site capable of being cleaved, e.g., a site which is recognized and cleaved by an enzyme; a nucleic acid encoding an altered site which is recognized and cleaved by an enzyme but is cleaved less efficiently than the site normally recognized by the enzyme.

In a preferred embodiment, when the product is produced as a fusion peptide having a site which is not capable of being cleaved, the site includes at least 1, 2, 3, 4, 5, 6, 8, 10 amino acids but preferably not more than 30 to 50 amino acids which are not recognized as a cleavage site by an enzyme, e.g., an endoprotease. For example, a site which is not capable of being cleaved can be a series of alanine residues, e.g., at least 1, 2, 3, 4, 5, 6, 8, or 10 alanine residues.

In a preferred embodiment, when the product is produced as a fusion peptide having a site which is capable of being cleaved, the site can include at least 1, 2, 3, 4, 5, 6, 8, 10 but preferably not more than 30 to 50 amino acids which are recognized as a cleavage site by an enzyme. A site capable of being cleaved can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, an enzyme which is preferentially expressed in a tissue or fluid recognizes the site capable of being cleaved. For example, the enzyme can be an enzyme preferentially expressed in blood. An example of a site recognized by an enzyme preferentially expressed in blood is a blood coagulation cleavage site, e.g., a blood coagulation factor Xa cleavage site, e.g., a site having the amino acid sequence $X_1$-$X_2$-Gly-Arg, wherein $X_1$ is Iso, Leu, Pro or Ala and $X_2$ is a Gly, Asp, Gln or Asn residue. Other blood coagulation cleavage sites are described, for example, in U.S. Pat. No. 6,010,883, the contents of which is incorporated herein by reference.

In preferred embodiment, when the product is produced as a fusion peptide, the fusion peptide includes an altered site which is recognized and cleaved by an enzyme but is cleaved less efficiently than the site normally recognized by the enzyme. For example, the site can be a cleavage site which is recognized by an enzyme, e.g., an endoprotease, but which has been modified such that the enzyme cleaves the site less efficiently than the unmodified cleavage site. The site can be modified such that at least 1, 2, 3, 4, 5, 6, 8, or 10 amino acids are substituted, deleted or added to the cleavage site. For example, a site having 1, 2, or 3 arginine(s) is less efficiently recognized by the endoprotease furin than a site having 4 or more arginine residues.

In a preferred embodiment, when the product is produced as a fusion peptide having a site capable of cleavage (e.g., a site which is cleaved by an enzyme or an altered site which is recognized by an enzyme but cleaved less efficiently than an unaltered site), the site is: part of the pro-region of a somatostatin nucleic acid sequence; part of the nucleic acid sequence of the small peptide; formed at the junction of the pro-region and the sequence encoding the small peptide; the site is cleaved such that the small peptide does not include any extraneous sequence; the site is cleaved such that the small peptide includes less than 10, 5, 4, 3, 2, or 1 extraneous amino acid residues.

In another preferred embodiment, the product is produced as a fusion peptide and there are no additional amino acids present between the pro-region and the small peptide.

In a preferred embodiment, the nucleic acid sequence encodes: the pro-region of human somatostatin or a functional fragment or sequence variant thereof; the pre-region of human somatostatin or a functional fragment thereof; the prepro-region of human somatostatin or a functional fragment or sequence variant thereof. In a preferred embodiment, the pre-, pro-, or prepro-region differs from wild-type by 1 but not more than 5, 10, 12, 25, 27, 30, 35, 40, 44, 48, 50 amino acid residues.

In a preferred embodiment, the product is a small peptide, e.g., a small human peptide, e.g., a small human hormone, e.g., a human anti-diabetogenic peptide, e.g., human GLP-1, e.g., GLP-1 (7-37), GLP-1 (7-36), or a fragment or variant thereof. In a preferred embodiment, the product is a protein, e.g., a human protein or functional fragment or variant thereof. In a preferred embodiment, the protein is: a secreted protein, e.g., a hormone, a growth factor, a neurotrophic factor, a binding protein, a cytokine, an angiogenic or antiangiogenic protein, a blood cell regulator. In a preferred embodiment, the protein is: leptin, calcitonin, growth hormone, agouti, agouti signaling protein, agouti-related protein, myostatin, fibroblast growth factor, epidermal growth factor, keratinocyte growth factor, transforming growth factor, hepatocyte growth factor, bone morphogenetic protein, nerve growth factor, neurotrophin, glial-derived neurotrophic factor, brain-derived neurotrophic factor, insulin-like growth factor binding protein, acid-labile subunit, tumor necrosis factor alpha, interleukins, interferons, vascular endothelial growth factor, angiostatin, endostatin, platelet-derived growth factor, granulocyte colony stimulating factor, erythropoeitin. In a preferred embodiment, the nucleic acid sequence encoding a product is a synthetic nucleic acid, e.g., a synthetic nucleic acid which encodes a product wherein at least one non-common or less common codon of the product has been replaced by a common codon.

In another aspect, the invention features, a cell having its genome modified to express a nucleic acid sequence, e.g., an endogenous genomic sequence encoding a product, e.g., a small peptide. The cell can be a cell which normally does not make or contain the product or can be a cell which normally makes or contains the product. For example, the cell can be a cell which makes or contains the product, e.g., the small peptide, but in lower quantities than normal (e.g., in quantities less than the physiologically normal levels) or in a defective form or a cell which makes the product, e.g., the small peptide, at physiologically normal levels, but is augmented to enhance the content or production of a product. The genome of the cell is modified by introducing an exogenous nucleic acid sequence which includes a nucleic acid sequence encoding the pro-region of a somatostatin or a functional fragment or sequence variant thereof. This sequence can be linked to a nucleic acid sequence within the genome of the cell which encodes a product, e.g., a small peptide, by for, for example, homologous recombination.

In a preferred embodiment, the nucleic acid sequence further encodes a signal peptide. In a preferred embodiment, the sequence encoding the signal peptide is from the pre-region of a somatostatin.

In a preferred embodiment, the cell is: a mammalian cell, e.g., a primary or secondary mammalian cell, e.g., a fibroblast, a hematopoietic stem cell, a myoblast, a keratinocyte, an epithelial cell, and endothelial cell, a glial cell, a neural cell, a cell comprising a formed element of the blood, a muscle cell and precursors of these somatic cells; a transformed or immortalized cell line; a cell other than an endocrine cell; one in which somatostatin is not normally expressed. Preferably, the cell is a human cell. Examples of immortalized human cell line useful in the present method include, but are not limited to: a Bowes Melanoma cell (ATCC Accession No. CRL 9607), a Daudi cell (ATCC Accession No. CCL 213), a HeLa cell and a derivative of a HeLa cell (ATCC Accession Nos. CCL 2 CCL2.1, and CCL 2.2), a HL-60 cell (ATCC Accession No. CCL 240), a HT1080 cell (ATCC Accession No. CCL 121), a Jurkat cell (ATCC Accession No. TIB 152), a KB carcinoma cell (ATCC Accession No. CCL 17), a K-562 leukemia cell (ATCC Accession No. CCL 243), a MCF-7 breast cancer cell (ATCC Accession No. BTH 22), a MOLT-4 cell (ATCC Accession No. 1582), a Nanalwa cell (ATCC Accession No. CRL 1432), a Rafji cell (ATCC Accession No. CCL 86), a RPMI 8226 cell (ATCC Accession No. CCL 155), a U-937 cell (ATCC Accession No. 1593), WI-38VA13 sub line 2R4 cells (ATCC Accession No. CLL 155), a CCRF-CEM cell (ATCC Accession No. CCL 119) and a 2780AD ovarian carcinoma cell (Van Der Blick et al., Cancer Res. 48:5927–5932, 1988), as well as heterohybridoma cells produced by fusion of human cells and cells of another species. In another embodiment, the immortalized cell line can be cell line other than a human cell line, e.g., a CHO cell line, a COS cell line.

In a preferred embodiment, additional regulatory sequences sufficient for expression of the exogenous nucleic acid sequence in the cell are also introduced. These regulatory sequences can be linked to the exogenous nucleic acid sequence. In a preferred embodiment, the regulatory sequence is a 5' regulatory sequence, e.g., a 5' flanking sequence (e.g., a promoter and/or an enhancer), and/or 5' untranslated region (5'UTR). The regulatory sequence can be a viral or a non-viral sequence. In a preferred embodiment, the regulatory sequence can be: the regulatory sequence that normally occurs with the product, the regulatory sequence of CMV, elastase, aldolase, or other constitutively active regulatory sequences; a glucose-responsive regulatory sequence, e.g., an insulin regulatory sequence; a regulatory sequence involved in feeding/satiety behavior, e.g., a leptin regulatory sequence.

In a preferred embodiment, the product is a small peptide. In a preferred embodiment, the small peptide is: a small hormone; an anti-diabetogenic peptide, e.g., an anti-diabetogenic peptide selected from the group consisting of glucagons-like peptide-1 (GLP-1), e.g., GLP-1 (7-37), GLP-1 (7-36), insulin, insulin-like growth factor-1, insulin-like growth factor-2, exendin-4, gastric inhibitory polypeptide and analogs thereof. In a preferred embodiment, the analog of GLP-1 is GLP-1-Gly-8.

In a preferred embodiment, the product is: a protein. In a preferred embodiment, the protein is: a secreted protein, e.g., a hormone, a growth factor, a neurotrophic factor, a binding protein, a cytokine, an angiogenic or antiangiogenic protein, a blood cell regulator. In a preferred embodiment, the protein is: leptin, calcitonin, growth hormone, agouti, agouti signaling protein, agouti-related protein, myostatin, fibroblast growth factor, epidermal growth factor, keratinocyte growth factor, transforming growth factor, hepatocyte growth factor, bone morphogenetic protein, nerve growth factor, neurotrophin, glial-derived neurotrophic factor, brain-derived neurotrophic factor, insulin-like growth factor binding protein, acid-labile subunit, tumor necrosis factor alpha, interleukins, interferons, vascular endothelial growth factor, angiostatin, endostatin, platelet-derived growth factor, granulocyte colony stimulating factor, erythropoeitin.

In a preferred embodiment, the exogenous nucleic acid sequence can introduce a site of cleavage. The integration of the exogenous nucleic acid sequence can give rise to a site between the pro-region and the sequence encoding the product at which the product can be cleaved from a precursor. In one embodiment, the product produced by the cell is in mature form, e.g., the product has been cleaved from the pro-somatostatin or functional fragment thereof, e.g., a small peptide is produced in cleaved form. The site can be: a nucleic acid sequence encoding a multibasic, dibasic or monobasic cleavage site; a nucleic acid sequence encoding an endoprotease cleavage site: a nucleic acid sequence encoding a cleavage site recognized by a pro-protein convertase, e.g., furin, PACE4, substilisin-related pro-protein convertase, PC1, PC2, PC6 or PC7. In a preferred embodiment, the site is: part of the pro-region of a somatostatin nucleic acid sequence; part of the nucleic acid sequence of the product, e.g., a small peptide; formed at the junction of the pro-region and the sequence encoding the product; a nucleic acid sequence encoding at least 1, 2, 3, 4, 5, 6, 8, 10 amino acid residues but preferably not more than 30 to 50 residues. In a preferred embodiment, the nucleic acid sequence encodes a multibasic cleavage site having the amino acid sequence Arg-Ala-Arg-Ala-Arg-Arg (SEQ ID NO:1). In another preferred embodiment, the nucleic acid sequence encodes a cleavage site having the amino acid sequence X-Arg-X-X-Arg. In a preferred embodiment, the site is cleaved such that the product does not include any extraneous sequence. In a preferred embodiment, the site is cleaved such that the product includes less than 10, 5, 4, 3, 2, or 1 extraneous amino acid residues.

In another preferred embodiment, the product produced by the cell is a fusion peptide, e.g., a fusion peptide which includes a pro-region of somatostatin or a functional fragment thereof and a small peptide.

In a preferred embodiment, when the product produced by the cell is a fusion peptide, there can be a site between the pro-region and the sequence encoding the product, e.g., the small peptide. The site can be a nucleic acid encoding at least 1, 2, 3, 4, 5, 6, 8, 10 amino acids but preferably not more than 30 to 50 amino acids. In a preferred embodiment, the site can be: a nucleic acid sequence encoding amino acids which are not cleaved, e.g., the site is not recognized by an enzyme capable of cleaving the site; a nucleic acid encoding a site capable of being cleaved, e.g., a site which is recognized and cleaved by an enzyme; a nucleic acid encoding an altered site which is recognized and cleaved by an enzyme but is cleaved less efficiently than the site normally recognized by the enzyme.

In a preferred embodiment, when the product is produced by the cell as a fusion peptide having a site which is not capable of being cleaved, the site includes at least 1, 2, 3, 4, 5, 6, 8, 10 amino acids but preferably not more than 30 to 50 amino acids which are not recognized as a cleavage site by an enzyme, e.g., an endoprotease. For example, a site which is not capable of being cleaved can be a series of alanine residues, e.g., at least 1, 2, 3, 4, 5, 6, 8, or 10 alanine residues.

In a preferred embodiment, when the product is produced by the cell as a fusion peptide having a site which is capable of being cleaved, the site can include at least 1, 2, 3, 4, 5, 6, 8, 10 but preferably not more than 30 to 50 amino acids which are recognized as a cleavage site by an enzyme. A site capable of being cleaved can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, an enzyme which is preferentially expressed in a tissue or fluid recognizes the site capable of being cleaved. For example, the enzyme can be an enzyme preferentially expressed in blood. An example of a site recognized by an enzyme preferentially expressed in blood is a blood coagulation cleavage site, e.g., a blood coagulation factor Xa cleavage site, e.g., a site having the amino acid sequence $X_1$-$X_2$-Gly-Arg, wherein $X_1$ is Iso, Leu, Pro or Ala and $X_2$ is a Gly, Asp, Gln or Asn residue. Other blood coagulation cleavage sites are described, for example, in U.S. Pat. No. 6,010,883, the contents of which is incorporated herein by reference.

In preferred embodiment, when the product is produced by the cell as a fusion peptide, the fusion peptide includes an altered site which is recognized and cleaved by an enzyme but is cleaved less efficiently than the site normally recognized by the enzyme. For example, the site can be a cleavage site which is recognized by an enzyme, e.g., an endoprotease, but which has been modified such that the enzyme cleaves the site less efficiently than the unmodified cleavage site. The site can be modified such that at least 1, 2, 3, 4, 5, 6, 8, or 10 amino acids are substituted, deleted or added to the cleavage site. For example, a site having 1, 2, or 3 arginine(s) is less efficiently recognized by the endoprotease furin than a site having 4 or more arginine residues.

In a preferred embodiment, when the product is produced by the cell as a fusion peptide having a site capable of cleavage (e.g., a site which is cleaved by an enzyme or an altered site which is recognized by an enzyme but cleaved less efficiently than an unaltered site), the site is: part of the pro-region of a somatostatin nucleic acid sequence; part of the nucleic acid sequence of the small peptide; formed at the junction of the pro-region and the sequence encoding the small peptide; the site is cleaved such that the small peptide does not include any extraneous sequence; the site is cleaved such that the small peptide includes less than 10, 5, 4, 3, 2, or 1 extraneous amino acid residues.

In another preferred embodiment, the product is produced by the cell as a fusion peptide and there are no additional amino acids present between the pro-region and the small peptide.

In a preferred embodiment, the nucleic acid sequence encodes: the pro-region of human somatostatin or a functional fragment or sequence variant thereof; the pre-region of human somatostatin or a functional fragment thereof; the prepro-region of human somatostatin or a functional fragment or sequence variant thereof. In a preferred embodiment, the pre-, pro-, or prepro-region differs from wild-type by 1 but not more than 5, 10, 12, 25, 27, 30, 35, 40, 44, 48, 50 amino acid residues. In a preferred embodiment, the nucleic acid sequence encoding a product, e.g., a small peptide, is a synthetic nucleic acid, e.g., a synthetic nucleic acid which encodes a small peptide wherein at least one non-common or less common codon of the peptide has been replaced by a common codon.

In another aspect, the invention features, a method of making a product, e.g., a small peptide. The method includes: providing a cell into which has been introduced a nucleic acid construct, e.g., a construct as described herein, which includes a nucleic acid sequence encoding a signal peptide, a nucleic acid sequence which encodes the pro-region of a somatostatin or a functional fragment or variant thereof, and a nucleic acid sequence encoding a product, e.g., a small peptide; and allowing the product to be expressed, to thereby obtain a product.

In a preferred embodiment, the nucleic acid sequence encoding the product, e.g., small peptide is a cDNA or a genomic sequence.

In a preferred embodiment, the cell is: a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells; a transformed or immortalized cell line; a cell other than an endocrine cell; one in which somatostatin is not normally expressed. Preferably, the cell is a human cell. Examples of immortalized human cell line useful in the present method include, but are not limited to: a Bowes Melanoma cell (ATCC Accession No. CRL 9607), a Daudi cell (ATCC Accession No. CCL 213), a HeLa cell and a derivative of a HeLa cell (ATCC Accession Nos. CCL2 CCL2.1, and CCL 2.2), a HL-60 cell (ATCC Accession No. CCL 240), a HT1080 cell (ATCC Accession No. CCL 121), a Jurkat cell (ATCC Accession No. TIB 152), a KB carcinoma cell (ATCC Accession No. CCL 17), a K-562 leukemia cell (ATCC Accession No. CCL 243), a MCF-7 breast cancer cell (ATCC Accession No. BTH 22), a MOLT-4 cell (ATCC Accession No. 1582), a Namalwa cell (ATCC Accession No. CRL 1432), a Rafji cell (ATCC Accession No. CCL 86), a RPMI 8226 cell (ATCC Accession No. CCL 155), a U-937 cell (ATCC Accession No. 1593), WI-28VA13 sub line 2R4 cells (ATCC Accession No. CLL 155), a CCRF-CEM cell (ATCC Accession No. CCL 119) and a 2780AD ovarian carcinoma cell (Van Der Blick et al., Cancer Res. 48:5927–5932, 1988), as well as heterohybridoma cells produced by fusion of human cells and cells of another species. In another embodiment the immortalized cell line can be cell line other than a human cell line, e.g., a CHO cell line, a COS cell line.

In a preferred embodiment the cell further includes at least one regulatory sequence, sufficient for expression of the exogenous nucleic acid sequence in the cell. In a preferred embodiment, the regulatory sequence is a 5' regulatory sequence, e.g., a 5' flanking sequence (e.g., a promoter and/or an enhancer), and/or 5' untranslated region (5'UTR); a 3' regulatory sequence, e.g., a 3' untranslated region (3'UTR) (e.g., a polyadenylation sequence) and/or a 3' flanking sequence; at least one splice junction site. The regulatory sequence can be a viral or a non-viral sequence. In a preferred embodiment, the regulatory sequence can be: the regulatory sequence that normally occurs with the product, e.g., the small peptide, the regulatory sequence of CMV, elastase, aldolase, or other constitutively active regulatory sequences; a glucose-responsive regulatory sequence, e.g., an insulin regulatory sequence; a regulatory sequence involved in feeding/satiety behavior, e.g., a leptin regulatory sequence.

In a preferred embodiment, the sequence encoding the signal peptide is from the pre-region of a somatostatin.

In a preferred embodiment, the product is a small peptide. In a preferred embodiment, the small peptide is: a small hormone; an anti-diabetogenic peptide, e.g., an anti-diabetic peptide is selected from the group consisting of glucagons-like peptide-1 (GLP-1), GLP-1 (7-37), GLP-1 (7-36), insulin, insulin-like growth factor-1, insulin-like growth factor-2, exendin-4, gastric inhibitory polypeptide and analogs thereof. In a preferred embodiment, the analog of GLP-1 is GLP-1-Gly-8. In a preferred embodiment, the small peptide is normally contained within a secretory vesicle within a cell.

In a preferred embodiment, the product, e.g., small peptide, is produced in mature form, e.g., the pro-region of somatostatin is cleaved from the small peptide. In a preferred embodiment, there is a site between the pro-region and the sequence encoding the small peptide at which the small peptide can be cleaved from a precursor. The site can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4 substilisin-related pro-protein convertase, PC1, PC2, PC6, or PC7. In a preferred embodiment, the site is: part of the pro-region of a somatostatin nucleic acid sequence; part of the nucleic acid sequence of the product, e.g., the small peptide; formed at the junction of the pro-region and the sequence encoding the product; a nucleic acid sequence encoding at least 1, 2, 3, 4, 5, 6, 8, 10 amino acid residues but preferably not more than 30 to 50 amino acid residues. In a preferred embodiment, the nucleic acid sequence encodes a multibasic cleavage site having the amino acid sequence Arg-Ala-Arg-Ala-Arg-Arg (SEQ ID NO:1). In another preferred embodiment, the nucleic acid sequence encodes a cleavage site having the amino acid sequence X-Arg-X-X-Arg. In a preferred embodiment, the site is cleaved such that the product does not include any extraneous sequence. In another preferred embodiment, the site is cleaved such that the product includes less than 10, 5, 4, 3, 2, or 1 extraneous amino acid residues.

In another preferred embodiment, the product, e.g., the small peptide, is produced as a fusion peptide, e.g., a fusion peptide which includes a pro-region of somatostatin or a functional fragment thereof and a small peptide.

In a preferred embodiment, when the small peptide is produced as a fusion peptide, there is a site between the pro-region and the sequence encoding the small peptide. The site can be a nucleic acid encoding at least 1, 2, 3, 4, 5, 6, 8, 10 amino acids but preferably not more than 30 to 50 amino acids. In a preferred embodiment, the site can be: a nucleic acid sequence encoding amino acids which are not cleaved, e.g., the site is not recognized by an enzyme capable of cleaving the site; a nucleic acid encoding a site capable of being cleaved, e.g., a site which is recognized and cleaved by an enzyme; a nucleic acid encoding an altered site which is recognized and cleaved by an enzyme but is cleaved less efficiently than the site normally recognized by the enzyme.

In a preferred embodiment, when the small peptide is produced as a fusion peptide having a site which is not capable of being cleaved, the site includes at least 1, 2, 3, 4, 5, 6, 8, 10 amino acids but preferably not more than 30 to 50 amino acids which are not recognized as a cleavage site by an enzyme, e.g., an endoprotease. For example, a site which is not capable of being cleaved can be a series of alanine residues, e.g., at least 1, 2, 3, 4, 5, 6, 8, or 10 alanine residues.

In a preferred embodiment, when the small peptide is produced as a fusion peptide having a site which is capable of being cleaved, the site can include at least 1, 2, 3, 4, 5, 6, 8, 10 but preferably not more than 30 to 50 amino acids which are recognized as a cleavage site by an enzyme. A site capable of being cleaved can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, an enzyme which is preferentially expressed in a tissue or fluid recognizes the site capable of being cleaved. For example, the enzyme can be an enzyme preferentially expressed in blood. An example of a site recognized by an enzyme preferentially expressed in blood is a blood coagulation cleavage site, e.g., a blood coagulation factor Xa cleavage site, e.g., a site having the amino acid sequence $X_1$-$X_2$-Gly-Arg, wherein $X_1$ is Iso, Leu, Pro or Ala and $X_2$ is a Gly, Asp, Gln or Asn residue. Other blood coagulation cleavage sites are described, for example, in U.S. Pat. No. 6,010,883, the contents of which is incorporated herein by reference.

In preferred embodiment, when the small peptide is produced as a fusion peptide, the fusion peptide includes an altered site which is recognized and cleaved by an enzyme but is cleaved less efficiently than the site normally recognized by the enzyme. For example, the site can be a cleavage site which is recognized by an enzyme, e.g., an endoprotease, but which has been modified such that the enzyme cleaves the site less efficiently than the unmodified cleavage site. The site can be modified such that at least 1, 2, 3, 4, 5, 6, 8, or 10 amino acids are substituted, deleted or added to the cleavage site. For example, a site having 1, 2, or 3 arginine(s) is less efficiently recognized by the endoprotease furin than a site having 4 or more arginine residues.

In a preferred embodiment, when the small peptide is produced as a fusion peptide having a site capable of cleavage (e.g., a site which is cleaved by an enzyme or an altered site which is recognized by an enzyme but cleaved less efficiently than an unaltered site), the site is: part of the pro-region of a somatostatin nucleic acid sequence; part of the nucleic acid sequence of the small peptide; formed at the junction of the pro-region and the sequence encoding the small peptide; the site is cleaved such that the small peptide does not include any extraneous sequence; the site is cleaved such that the small peptide includes less than 10, 5, 4, 3, 2, or 1 extraneous amino acid residues.

In another preferred embodiment, the small peptide is produced as a fusion peptide and there are no additional amino acids present between the pro-region and the small peptide.

In a preferred embodiment, the nucleic acid sequence encodes: the pro-region of human somatostatin or a functional fragment or sequence variant thereof; the pre-region of human somatostatin or a functional fragment thereof; the prepro-region of human somatostatin or a functional fragment or sequence variant thereof. In a preferred embodiment, the pre-, pro-, or prepro-region differs from wild-type by 1 but not more than 5, 10, 12, 25, 27, 30, 35, 40, 44, 48, 50 amino acid residues.

In a preferred embodiment, the small peptide is a human small peptide, e.g., a human small hormone, e.g., a human anti-diabetogenic peptide, e.g., human GLP-1 or a fragment or variant thereof. In a preferred embodiment, the product is a human protein or functional fragment or variant thereof. In a preferred embodiment, the protein is: a secreted protein, e.g., a hormone, a growth factor, a neurotrophic factor, a binding protein, a cytokine, an angiogenic or antiangiogenic protein, a blood cell regulator. In a preferred embodiment, the protein is: leptin, calcitonin, growth hormone, agouti, agouti signaling protein, agouti-related protein, myostatin, fibroblast growth factor, epidermal growth factor, keratinocyte growth factor, transforming growth factor, hepatocyte growth factor, bone morphogenetic protein, nerve growth factor, neurotrophin, glial-derived neurotrophic factor, brain-derived neurotrophic factor, insulin-like growth factor binding protein, acid-labile subunit, tumor necrosis factor alpha, interleukins, interferons, vascular endothelial growth factor, angiostatin, endostatin, platelet-derived growth factor, granulocyte colony stimulating factor, erythropoeitin. In a preferred embodiment, the nucleic acid sequence encoding a product is a synthetic nucleic acid, e.g., a synthetic nucleic which encodes a product wherein at least one non-common or less common codon of the product has been replaced by a common codon.

In a preferred embodiment, the product, e.g., the small peptide is produced in the body of the subject, e.g., a subject having a disorder characterized by a deficiency of the product. In a preferred embodiment, the product, e.g., the small peptide is produced in an isolated cell.

In another aspect, the invention features, a method of making a genetically engineered cell capable of expressing a product, e.g., the small peptide. The method includes providing a cell; and introducing into the cell a nucleic acid construct, e.g., a construct as described herein, which includes a nucleic acid sequence encoding a signal peptide, a nucleic acid sequence which encodes the pro-region of a somatostatin or a functional fragment or variant thereof, and a nucleic acid sequence encoding a product, e.g., the small peptide, to thereby obtain a genetically engineered cell capable of expressing a product, e.g., a small peptide.

In a preferred embodiment, the nucleic acid sequence encoding the product is a cDNA or a genomic sequence.

In a preferred embodiment, the cell is: a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells; a transformed or immortalized cell line; a cell other than an endocrine cell; one in which somatostatin is not normally expressed. Preferably, the cell is a human cell. Examples of immortalized human cell line useful in the present method include, but are not limited to: a Bowes Melanoma cell (ATCC Accession No. CRL 9607), a Daudi cell (ATCC Accession No. CCL 213), a HeLa cell and a derivative of a HeLa cell (ATCC Accession Nos. CCL2 CCL2.1, and CCL 2.2), a HL-60 cell (ATCC Accession No. CCL 240), a HT1080 cell (ATCC Accession No. CCL 121), a Jurkat cell (ATCC Accession No. TIB 152), a KB carcinoma cell (ATCC Accession No. CCL 17), a K-562 leukemia cell (ATCC Accession No. CCL 243), a MCF-7 breast cancer cell (ATCC Accession No. BTH 22), a MOLT-4 cell (ATCC Accession No. 1582), a Namalwa cell (ATCC Accession No. CRL 1432), a Rafji cell (ATCC Accession No. CCL 86), a RPMI 8226 cell (ATCC Accession No. CCL 155), a U-937 cell (ATCC Accession No. 1593), WI-28VA13 sub line 2R4 cells (ATCC Accession No. CLL 155), a CCRF-CEM cell (ATCC Accession No. CCL 119) and a 2780AD ovarian carcinoma cell (Van Der Blick et al., Cancer Res. 48:5927–5932, 1988), as well as heterohybridoma cells produced by fusion of human cells and cells of another species. In another embodiment, the immortalized cell line can be cell line other than a human cell line, e.g., a CHO cell line, a COS cell line.

In a preferred embodiment the cell further includes at least one regulatory sequence, sufficient for expression of the exogenous nucleic acid sequence in the cell. In a preferred embodiment, the regulatory sequence is a 5' regulatory sequence, e.g., a 5' flanking sequence (e.g., a promoter and/or an enhancer), and/or 5' untranslated region (5'UTR); a 3' regulatory sequence, e.g., a 3' untranslated region (3'UTR) (e.g., a polyadenylation sequence) and/or a 3' flanking sequence; at least one splice junction site. The regulatory sequence can be a viral or a non-viral sequence. In a preferred embodiment, the regulatory sequence can be: the regulatory sequence that normally occurs with the product, e.g., the small peptide, the regulatory sequence of CMV, elastase, aldolase, or other constitutively active regulatory sequences; a glucose-responsive regulatory sequence, e.g., an insulin regulatory sequence; a regulatory sequence involved in feeding/satiety behavior, e.g., a leptin regulatory sequence.

In a preferred embodiment, the product is a small peptide. In a preferred embodiment, the sequence encoding the signal peptide is from the pre-region of a somatostatin.

In a preferred embodiment, the small peptide is: a small hormone; an anti-diabetogenic peptide, e.g., an anti-diabetic peptide is selected from the group consisting of glucagons-like peptide-1 (GLP-1), GLP-1 (7-37), GLP-1 (7-36), exendin-4, gastric inhibitory polypeptide and analogs thereof. In a preferred embodiment, the analog of GLP-1 is GLP-1Gly8.

In a preferred embodiment, the small peptide is normally contained within a secretory vesicle within a cell.

In a preferred embodiment, the product, e.g., small peptide, is produced in mature form, e.g., the pro-region of somatostatin is cleaved from the small peptide. In a preferred embodiment, there is a site between the pro-region and the sequence encoding the small peptide at which the small peptide can be cleaved from a precursor. The site can be: a nucleic acid sequence encoding a multibasic, dibasic or monobasic cleavage site; a nucleic acid sequence encoding an endoprotease cleavage site; a nucleic acid sequence encoding an endoprotease cleavage site; a nucleic acid sequence encoding a cleavage site recognized by a pro-protein convertase, e.g., furin, substilisin-related pro-protein convertase, PC1, or PC2. In a preferred embodiment, the site is: part of the pro-region of a somatostatin nucleic acid sequence; part of the nucleic acid sequence of product, e.g., the small peptide; formed at the junction of the pro-region and the sequence encoding the product; a nucleic acid sequence encoding at least 1, 2, 3, 4, 5, 6, 8, 10 amino acid residues but preferably not more than 30 to 50 amino acid residues. In a preferred embodiment, the nucleic acid sequence encodes a multibasic cleavage site having the amino acid sequence Arg-Ala-Arg-Ala-Arg-Arg (SEQ ID NO:1). In another preferred embodiment, the nucleic acid sequence encodes a cleavage site having the amino acid sequence X-Arg-X-X-Arg. In a preferred embodiment, the site is cleaved such that the product does not include any extraneous sequence. In another preferred embodiment, the site is cleaved such that the product includes less than 10, 5, 4, 3, 2, or 1 extraneous amino acid residues.

In another preferred embodiment, the product, e.g., a small peptide, is produced as a fusion peptide, e.g., a fusion peptide which includes a pro-region of somatostatin or a functional fragment thereof and a small peptide.

In a preferred embodiment, when the small peptide is produced as a fusion peptide, there is a site between the pro-region and the sequence encoding the small peptide. The site can be a nucleic acid encoding at least 1, 2, 3, 4, 5, 6, 8, 10 amino acids but preferably not more than 30 to 50 amino acids. In a preferred embodiment, the site can be: a nucleic acid sequence encoding amino acids which are not cleaved, e.g., the site is not recognized by an enzyme capable of cleaving the site; a nucleic acid encoding a site capable of being cleaved, e.g., a site which is recognized and cleaved by an enzyme; a nucleic acid encoding an altered site which is recognized and cleaved by an enzyme but is cleaved less efficiently than the site normally recognized by the enzyme.

In a preferred embodiment, when the small peptide is produced as a fusion peptide having a site which is not capable of being cleaved, the site includes at least 1, 2, 3, 4, 5, 6, 8, 10 amino acids but preferably not more than 30 to 50 amino acids which are not recognized as a cleavage site by an enzyme, e.g., an endoprotease. For example, a site which is not capable of being cleaved can be a series of alanine residues, e.g., at least 1, 2, 3, 4, 5, 6, 8, or 10 alanine residues.

In a preferred embodiment, when the small peptide is produced as a fusion peptide having a site which is capable of being cleaved, the site can include at least 1, 2, 3, 4, 5, 6, 8, 10 but preferably not more than 30 to 50 amino acids which are recognized as a cleavage site by an enzyme. A site capable of being cleaved can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, an enzyme which is preferentially expressed in a tissue or fluid recognizes the site capable of being cleaved. For example, the enzyme can be an enzyme preferentially expressed in blood. An example of a site recognized by an enzyme preferentially expressed in blood is a blood coagulation cleavage site, e.g., a blood coagulation factor Xa cleavage site, e.g., a site having the amino acid sequence $X_1$-$X_2$-Gly-Arg, wherein $X_1$ is Iso, Leu, Pro or Ala and $X_2$ is a Gly, Asp, Gln or Asn residue. Other blood coagulation cleavage sites are described, for example, in U.S. Pat. No. 6,010,883, the contents of which is incorporated herein by reference.

In preferred embodiment, when the small peptide is produced as a fusion peptide, the fusion peptide includes an altered site which is recognized and cleaved by an enzyme but is cleaved less efficiently than the site normally recognized by the enzyme. For example, the site can be a cleavage site which is recognized by an enzyme, e.g., an endoprotease, but which has been modified such that the enzyme cleaves the site less efficiently than the unmodified cleavage site. The site can be modified such that at least 1, 2, 3, 4, 5, 6, 8, or 10 amino acids are substituted, deleted or added to the cleavage site. For example, a site having 1, 2, or 3 arginine(s) is less efficiently recognized by the endoprotease furin than a site having 4 or more arginine residues.

In a preferred embodiment, when the small peptide is produced as a fusion peptide having a site capable of cleavage (e.g., a site which is cleaved by an enzyme or an altered site which is recognized by an enzyme but cleaved less efficiently than an unaltered site), the site is: part of the pro-region of a somatostatin nucleic acid sequence; part of the nucleic acid sequence of the small peptide; formed at the junction of the pro-region and the sequence encoding the small peptide; the site is cleaved such that the small peptide does not include any extraneous sequence; the site is cleaved such that the small peptide includes less than 10, 5, 4, 3, 2, or 1 extraneous amino acid residues.

In another preferred embodiment, the small peptide is produced as a fusion peptide and there are no additional amino acids present between the pro-region and the small peptide.

In a preferred embodiment, the nucleic acid sequence encodes: the pro-region of human somatostatin or a functional fragment or sequence variant thereof; the pre-region of human somatostatin or a functional fragment thereof; the prepro-region of human somatostatin or a functional fragment or sequence variant thereof. In a preferred embodiment, the pre-, pro-, or prepro-region differs from wild-type by 1 but not more than 5, 10, 12, 25, 27, 30, 35, 40, 44, 48, 50 amino acid residues.

In a preferred embodiment, the small peptide is a human small peptide, e.g., a human small hormone, e.g., a human anti-diabetogenic peptide, e.g., human GLP-1 or a fragment or variant thereof. In a preferred embodiment, the product is a human protein or functional fragment or variant thereof. In a preferred embodiment, the protein is: a secreted protein, e.g., a hormone, a growth factor, a neurotrophic factor, a binding protein, a cytokine, an angiogenic or antiangiogenic protein, a blood cell regulator. In a preferred embodiment, the protein is: leptin, calcitonin, growth hormone, agouti, agouti signaling protein, agouti-related protein, myostatin, fibroblast growth factor, epidermal growth factor, keratinocyte growth factor, transforming growth factor, hepatocyte growth factor, bone morphogenetic protein, nerve growth factor, neurotrophin, glial-derived neurotrophic factor, brain-derived neurotrophic factor, insulin-like growth factor binding protein, acid-labile subunit, tumor necrosis factor alpha, interleukins, interferons, vascular endothelial growth factor, angiostatin, endostatin, platelet-derived growth factor, granulocyte colony stimulating factor, erythropoeitin. In a preferred embodiment, the nucleic acid sequence encoding a product is a synthetic nucleic acid, e.g., a synthetic nucleic acid which encodes a product wherein at least one non-common or less common codon of the product has been replaced by a common codon.

In a preferred embodiment, the cell is provided by a subject to whom the genetically engineered cell will be administered. Other sources for providing a cell include a cell obtained from a donor other than the subject to whom the genetically engineered cell will be administered. The donor can be of the same species as the recipient subject (allogeneic) or a different species (xenogeneic).

In another aspect, the invention features a method of making a genetically engineered cell capable of expressing a product, e.g., a small peptide. The method includes providing a cell; and modifying the genome of a cell to express a nucleic acid sequence, e.g., an endogenous genomic sequence, encoding a product, e.g., a small peptide, e.g., a small peptide other than somatostatin. The cell can be one which normally does not make or contain the product or the cell can be one which normally makes or contains the product. For example, the cell can be a cell which makes or contains the product, e.g., the small peptide but in lower quantities than normal (e.g., in quantities less than the physiologically normal levels) in a defective form or a cell which makes the product at physiologically normal levels, but is augmented to enhance the content or production of a small peptide. The genome of the cell is modified by introducing an exogenous nucleic acid sequence which encodes the pro-region of a somatostatin or a functional fragment or variant thereof. This sequence can be linked to a nucleic acid sequence within the genome of the cell which encodes a product, e.g., a small peptide.

In a preferred embodiment, the exogenous nucleic acid sequence further encodes a signal peptide. In a preferred embodiment, the sequence encoding the signal peptide is from the pre-region of a somatostatin.

In a preferred embodiment, the cell is: a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells; a transformed or immortalized cell line; a cell other than an endocrine cell; one in which somatostatin is not normally expressed. Preferably, the cell is a human cell. Examples of immortalized human cell line useful in the present method include, but are not limited to: Bowes Melanoma cell (ATCC Accession No. CRL 9607), a Daudi cell (ATCC Accession No. CCL 213), a HeLa cell and a derivative of a HeLa cell (ATCC Accession Nos. CCL2 CCL2.1, and CCL 2.2), a HL-60 cell (ATCC Accession No. CCL 240), a HT1080 cell (ATCC Accession No. CCL 121), a Jurkat cell (ATCC Accession No. TIB 152), a KB carcinoma cell (ATCC Accession No. CCL 17), a K-562 leukemia cell (ATCC Accession No. CCL 243), a MCF-7 breast cancer cell (ATCC Accession No. BTH 22), a MOLT-4 cell (ATCC Accession No. 1582), a Namalwa cell (ATCC Accession No. CRL 1432), a Rafji cell (ATCC Accession No. CCL 86), a RPMI 8226 cell (ATCC Accession No. CCL 155), a U-937 cell (ATCC Accession No. 1593), WI-28VA13 sub line 2R4 cells (ATCC Accession No. CLL 155), a CCRF-CEM cell (ATCC Accession No. CCL 119) and a 2780AD ovarian carcinoma cell (Van Der Blick et al., Cancer Res. 48:5927–5932, 1988), as well as heterohybridoma cells produced by fusion of human cells and cells of another species. In another embodiment, the immortalized cell line can be cell line other than a human cell line, e.g., a CHO cell line, a COS cell line.

In a preferred embodiment, additional regulatory sequences sufficient for expression of the exogenous nucleic acid sequence in the cell are also introduced. These regulatory sequences can be linked to the exogenous nucleic acid sequence. In a preferred embodiment, the regulatory sequence is a 5' regulatory sequence, e.g., a 5' flanking sequence (e.g., a promoter and/or an enhancer), and/or 5' untranslated region (5'UTR). The regulatory sequence can be a viral or a non-viral sequence. In a preferred embodiment, the regulatory sequence can be: the regulatory sequence that normally occurs with the product, e.g., the small peptide, the regulatory sequence of CMV, elastase, aldolase, or other constitutively active regulatory sequences; a glucose-responsive regulatory sequence, e.g., an insulin regulatory sequence; a regulatory sequence involved in feeding/satiety behavior, e.g., a leptin regulatory sequence.

In a preferred embodiment, the product is a small peptide. In a preferred embodiment, the small peptide is: a small hormone; an anti-diabetogenic peptide, e.g., an anti-diabetogenic peptide selected from the group consisting of glucagon-like peptide-1 (GLP-1), e.g., GLP-1 (7-37), GLP-1 (7-36), insulin, insulin-like growth factor-1, insulin-like growth factor-2, exendin-4, gastric inhibitory polypeptide and analogs thereof. In a preferred embodiment, the analog of GLP-1 is GLP-1-Gly8.

In a preferred embodiment, the small peptide is normally contained within a secretory vesicle within a cell.

In a preferred embodiment, the product is a protein, e.g., a human protein.

In a preferred embodiment, the exogenous nucleic acid sequence can introduce a site of cleavage. The integration of the exogenous sequence can give rise to a site between the pro-region and the sequence encoding the product at which the product can be cleaved from a precursor. In one embodiment, the product produced by the cell is in mature form, e.g., the product has been cleaved from the pro-somatostatin or functional fragment thereof, e.g., a small peptide is produced in cleaved form. The site can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, the site is: part of the pro-region of a somatostatin nucleic acid sequence; part of the nucleic acid sequence of the product, e.g., the small peptide; formed at the junction of the pro-region and the sequence encoding the product; a nucleic acid sequence encoding at least 1, 2, 3, 4, 5, 6, 8, 10 amino acid residues but preferably not more than 30 to 50 residues. In a preferred embodiment, the nucleic acid sequence encodes a multibasic cleavage site having the amino acid sequence Arg-Ala-Arg-Ala-Arg-Arg (SEQ ID NO:1). In another preferred embodiment, the nucleic acid sequence encodes a cleavage site having the amino acid sequence X-Arg-X-X-Arg. In a preferred embodiment, the site is cleaved such that the product does not include any extraneous sequence. In another preferred embodiment, the site is cleaved such that the product includes less than 10, 5, 4, 3, 2, or 1 extraneous amino acid residues.

In another preferred embodiment, the product produced by the cell is a fusion peptide, e.g., a fusion peptide which includes a pro-region of somatostatin or a functional fragment thereof and a small peptide.

In a preferred embodiment, when the product produced by the cell is a fusion peptide, there can be a site between the pro-region and the sequence encoding the product, e.g., the small peptide. The site can be a nucleic acid encoding at least 1, 2, 3, 4, 5, 6, 8, 10 amino acids but preferably not more than 30 to 50 amino acids. In a preferred embodiment, the site can be: a nucleic acid sequence encoding amino acids which are not cleaved, e.g., the site is not recognized by an enzyme capable of cleaving the site; a nucleic acid encoding a site capable of being cleaved, e.g., a site which is recognized and cleaved by an enzyme; a nucleic acid encoding an altered site which is recognized and cleaved by an enzyme but is cleaved less efficiently than the site normally recognized by the enzyme.

In a preferred embodiment, when the product is produced by the cell as a fusion peptide having a site which is not capable of being cleaved, the site includes at least 1, 2, 3, 4, 5, 6, 8, 10 amino acids but preferably not more than 30 to 50 amino acids which are not recognized as a cleavage site by an enzyme, e.g., an endoprotease. For example, a site which is not capable of being cleaved can be a series of alanine residues, e.g., at least 1, 2, 3, 4, 5, 6, 8, or 10 alanine residues.

In a preferred embodiment, when the product is produced by the cell as a fusion peptide having a site which is capable of being cleaved, the site can include at least 1, 2, 3, 4, 5, 6, 8, 10 but preferably not more than 30 to 50 amino acids which are recognized as a cleavage site by an enzyme. A site capable of being cleaved can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, an enzyme which is preferentially expressed in a tissue or fluid recognizes the site capable of being cleaved. For example, the enzyme can be an enzyme preferentially expressed in blood. An example of a site recognized by an enzyme preferentially expressed in blood is a blood coagulation cleavage site, e.g., a blood coagulation factor Xa cleavage site, e.g., a site having the amino acid sequence $X_1$-$X_2$-Gly-Arg, wherein $X_1$ is Iso, Leu, Pro or Ala and $X_2$ is a Gly, Asp, Gln or Asn residue. Other blood coagulation cleavage sites are described, for example, in U.S. Pat. No. 6,010,883, the contents of which is incorporated herein by reference.

In preferred embodiment, when the product is produced by the cell as a fusion peptide, the fusion peptide includes an altered site which is recognized and cleaved by an enzyme but is cleaved less efficiently than the site normally recognized by the enzyme. For example, the site can be a cleavage site which is recognized by an enzyme, e.g., an endoprotease, but which has been modified such that the enzyme cleaves the site less efficiently than the unmodified cleavage site. The site can be modified such that at least 1, 2, 3, 4, 5, 6, 8, or 10 amino acids are substituted, deleted or added to the cleavage site. For example, a site having 1, 2, or 3 arginine(s) is less efficiently recognized by the endoprotease furin than a site having 4 or more arginine residues.

In a preferred embodiment, when the product is produced by the cell as a fusion peptide having a site capable of cleavage (e.g., a site which is cleaved by an enzyme or an altered site which is recognized by an enzyme but cleaved less efficiently than an unaltered site), the site is: part of the pro-region of a somatostatin nucleic acid sequence; part of the nucleic acid sequence of the small peptide; formed at the junction of the pro-region and the sequence encoding the small peptide; the site is cleaved such that the small peptide does not include any extraneous sequence; the site is cleaved such that the small peptide includes less than 10, 5, 4, 3, 2, or 1 extraneous amino acid residues.

In another preferred embodiment, the product is produced by the cell as a fusion peptide and there are no additional amino acids present between the pro-region and the small peptide.

In a preferred embodiment, the nucleic acid sequence encodes: the pro-region of human somatostatin or a functional fragment or sequence variant thereof; the pre-region of human somatostatin or a functional fragment thereof; the prepro-region of human somatostatin or a functional fragment or sequence variant thereof. In a preferred embodiment, the pre-, pro-, or prepro-region differs from wild-type by 1 but not more than 5, 10, 12, 25, 27, 30, 35, 40, 44, 48, 50 amino acid residues. In a preferred embodiment, the nucleic acid sequence encoding a product, e.g., a small peptide, is a synthetic nucleic acid, e.g., a synthetic nucleic acid which encodes a small peptide wherein at least one non-common or less common codon of the peptide has been replaced by a common codon.

In a preferred embodiment, the cell is provided by a subject to whom the genetically engineered cell will be administered. Other sources for providing a cell include a cell obtained from a donor other than the subject to whom the genetically engineered cell will be administered. The donor can be of the same species as the recipient subject (allogeneic) or a different species (xenogeneic).

In another aspect, the invention features a method of providing a small peptide to a subject. The method includes: administering to the subject an exogenous nucleic acid sequence, e.g., one described herein, which includes a nucleic acid sequence encoding a signal peptide, a nucleic acid sequence which encodes the pro-region of a somatostatin or a fragment or variant thereof, and a nucleic acid sequence encoding a small peptide, such that the small peptide is expressed in the subject.

In a preferred embodiment, the subject is a human.

In a preferred embodiment, the small peptide is provided to treat a subject, e.g., a subject having a disorder characterized by a deficiency of a small peptide. In a preferred embodiment, the disorder is a disorder characterized by decreased expression of a small peptide.

In a preferred embodiment, the nucleic acid sequence encoding the small peptide is a cDNA or a genomic sequence.

In a preferred embodiment, the sequence encoding the signal peptide is from the pre-region of a somatostatin.

In a preferred embodiment, the small peptide is: a small hormone; an anti-diabetogenic peptide, e.g., an anti-diabetogenic peptide selected from the group consisting of glucagon-like peptide-1 (GLP-1), e.g., GLP-1 (7-37), GLP-1 (7-36), insulin, insulin-like growth factor-1, insulin-like growth factor-2, exendin-4, gastric inhibitory polypeptide and analogs thereof. In a preferred embodiment, the analog of GLP-1 is GLP-1-Gly8.

In a preferred embodiment, the nucleic acid further includes at least one regulatory sequence. In a preferred embodiment, the regulatory sequence is a 5' regulatory sequence, e.g., a 5' flanking sequence (e.g., a promoter and/or an enhancer), and/or 5' untranslated region (5' UTR); a 3' regulatory sequence, e.g., a 3' untranslated region (3' UTR) (e.g., a polyadenylation sequence), a 3' flanking sequence; at least one splice junction. The regulatory sequence can be a viral or a non-viral sequence. In a preferred embodiment, the regulatory sequence can be: the regulatory sequence that normally occurs with the small peptide; the regulatory sequence of CMV, elastase, aldolase, or other constitutively active regulatory sequences; a glucose-responsive regulatory sequence, e.g., an insulin regulatory sequence; a regulatory sequence involved in feeding/satiety behavior, e.g., a leptin regulatory sequence.

In a preferred embodiment, the small peptide is an anti-diabetogenic peptide and the subject has diabetes.

In a preferred embodiment, the small peptide is produced in mature form, e.g., the pro-region of somatostatin is cleaved from the small peptide. In a preferred embodiment, there is a site between the pro-region and the sequence encoding the small peptide at which the small peptide can be cleaved from a precursor. The site is: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, the site is: part of the pro-region of a somatostatin nucleic acid sequence; part of the nucleic acid sequence of the small peptide; formed at the junction of the pro-region and the sequence encoding the small peptide; a nucleic acid sequence encoding at least 1, 2, 3, 4, 5, 6, 8, 10 amino acid residues but preferably not more than 30 to 50 residues. In a preferred embodiment, the nucleic acid sequence encodes a multibasic cleavage site having the amino acid sequence Arg-Ala-Arg-Ala-Arg-Arg (SEQ ID NO:1). In another preferred embodiment, the nucleic acid sequence encodes a cleavage site having the amino acid sequence X-Arg-X-X-Arg. In a preferred embodiment, the site is cleaved such that the small peptide does not include any extraneous sequence. In another preferred embodiment, the site is cleaved such that the small peptide includes less than 10, 5, 4, 3, 2, or 1 extraneous amino acid residue.

In another preferred embodiment, the product, e.g., a small peptide, is produced as a fusion peptide, e.g., a fusion peptide which includes a pro-region of somatostatin or a functional fragment thereof and a small peptide.

In a preferred embodiment, when the small peptide is produced as a fusion peptide, there is a site between the pro-region and the sequence encoding the small peptide. The site can be a nucleic acid encoding at least 1, 2, 3, 4, 5, 6, 8, 10 amino acids but preferably not more than 30 to 50 amino acids. In a preferred embodiment, the site can be: a nucleic acid sequence encoding amino acids which are not cleaved, e.g., the site is not recognized by an enzyme capable of cleaving the site; a nucleic acid encoding a site capable of being cleaved, e.g., a site which is recognized and cleaved by an enzyme; a nucleic acid encoding an altered site which is recognized and cleaved by an enzyme but is cleaved less efficiently than the site normally recognized by the enzyme.

In a preferred embodiment, when the small peptide is produced as a fusion peptide having a site which is not capable of being cleaved, the site includes at least 1, 2, 3, 4, 5, 6, 8, 10 amino acids but preferably not more than 30 to 50 amino acids which are not recognized as a cleavage site by an enzyme, e.g., an endoprotease. For example, a site which is not capable of being cleaved can be a series of alanine residues, e.g., at least 1, 2, 3, 4, 5, 6, 8, or 10 alanine residues.

In a preferred embodiment, when the small peptide is produced as a fusion peptide having a site which is capable of being cleaved, the site can include at least 1, 2, 3, 4, 5, 6, 8, 10 but preferably not more than 30 to 50 amino acids which are recognized as a cleavage site by an enzyme. A site capable of being cleaved can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, an enzyme which is preferentially expressed in a tissue or fluid recognizes the site capable of being cleaved. For example, the enzyme can be an enzyme preferentially expressed in blood. An example of a site recognized by an enzyme preferentially expressed in blood is a blood coagulation cleavage site, e.g., a blood coagulation factor Xa cleavage site, e.g., a site having the amino acid sequence $X_1$-$X_2$-Gly-Arg, wherein $X_1$ is Iso, Leu, Pro or Ala and $X_2$ is a Gly, Asp, Gln or Asn residue. Other blood coagulation cleavage sites are described, for example, in U.S. Pat. No. 6,010,883, the contents of which is incorporated herein by reference.

In preferred embodiment, when the small peptide is produced as a fusion peptide, the fusion peptide includes an altered site which is recognized and cleaved by an enzyme but is cleaved less efficiently than the site normally recognized by the enzyme. For example, the site can be a cleavage site which is recognized by an enzyme, e.g., an endoprotease, but which has been modified such that the enzyme cleaves the site less efficiently than the unmodified cleavage site. The site can be modified such that at least 1, 2, 3, 4, 5, 6, 8, or 10 amino acids are substituted, deleted or added to the cleavage site. For example, a site having 1, 2, or 3 arginine(s) is less efficiently recognized by the endoprotease furin than a site having 4 or more arginine residues.

In a preferred embodiment, when the small peptide is produced as a fusion peptide having a site capable of cleavage (e.g., a site which is cleaved by an enzyme or an altered site which is recognized by an enzyme but cleaved less efficiently than an unaltered site), the site is: part of the pro-region of a somatostatin nucleic acid sequence; part of the nucleic acid sequence of the small peptide; formed at the junction of the pro-region and the sequence encoding the small peptide; the site is cleaved such that the small peptide does not include any extraneous sequence; the site is cleaved such that the small peptide includes less than 10, 5, 4, 3, 2, or 1 extraneous amino acid residues.

In another preferred embodiment, the small peptide is produced as a fusion peptide and there are no additional amino acids present between the pro-region and the small peptide.

In a preferred embodiment, the nucleic acid sequence encodes: the pro-region of human somatostatin or a functional fragment or sequence variant thereof; the pre-region of human somatostatin or a functional fragment thereof; the prepro-region of human somatostatin or a functional fragment or sequence variant thereof. In a preferred embodiment, the pre-, pro-, or prepro-region differs from wild-type by 1 but not more than 5, 10, 12, 25, 27, 30, 35, 40, 44, 48, 50 amino acid residues.

In a preferred embodiment, the small peptide is a human small peptide, e.g., a human small hormone, e.g., a human anti-diabetogenic peptide, e.g., human GLP-1, e.g., GLP-1 (7-37), GLP-1 (7-36), or a fragment or variant thereof. In a preferred embodiment, the nucleic acid sequence encoding a small peptide is a synthetic nucleic acid, e.g., a synthetic nucleic acid which encodes a small peptide wherein at least one non-common or less common codon of the peptide has been replaced by a common codon.

Another aspect of the invention features a method of treating a subject having diabetes. The method includes: administering to a subject having diabetes an exogenous nucleic acid sequence, e.g., one described herein, which includes a nucleic acid sequence encoding a signal peptide, a nucleic acid sequence which encodes the pro-region of a somatostatin or a functional fragment or variant thereof, and a nucleic acid sequence encoding an anti-diabetogenic peptide, such that the anti-diabetogenic peptide is expressed.

In a preferred embodiment, the subject is a human.

In a preferred embodiment, the nucleic acid sequence encoding the anti-diabetogenic peptide is a cDNA or a genomic sequence.

In a preferred embodiment, the sequence encoding the signal peptide is from the pre-region of a somatostatin.

In a preferred embodiment, the nucleic acid further includes at least one regulatory sequence. In a preferred embodiment, the regulatory sequence is a 5' regulatory sequence, e.g., a 5' flanking sequence (e.g., a promoter and/or an enhancer), and/or 5' untranslated region (5' UTR); a 3' regulatory sequence, e.g., a 3' untranslated region (3' UTR) (e.g., a polyadenylation sequence), a 3' flanking sequence; at least one splice junction. The regulatory sequence can be a viral or a non-viral sequence. In a preferred embodiment, the regulatory sequence can be: the regulatory sequence that normally occurs with the small peptide; the regulatory sequence of CMV, elastase, aldolase, or other constitutively active regulatory sequences; a glucose-responsive regulatory sequence, e.g., an insulin regulatory sequence; a regulatory sequence involved in feeding/satiety behavior, e.g., a leptin regulatory sequence.

In a preferred embodiment, the anti-diabetogenic peptide is an anti-diabetogenic selected from the group consisting of glucagon-like peptide-1 (GLP-1), e.g., GLP-1 (7-37), GLP-1 (7-36), insulin, insulin-like growth factor-1, insulin-like growth factor-2, exendin-4, gastric inhibitory polypeptide and analogs thereof. In a preferred embodiment, the analog of GLP-1 is GLP-1-Gly8.

In a preferred embodiment, the anti-diabetogenic peptide is produced in mature form, e.g., the pro-region of somatostatin is cleaved from the anti-diabetogenic peptide. In a preferred embodiment, there is a site between the pro-region and the sequence encoding the anti-diabetogenic peptide at which the peptide can be cleaved from a precursor. The site can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, the site is: part of the pro-region of a somatostatin nucleic acid sequence; part of the nucleic acid sequence of the small peptide; formed at the junction of the pro-region and the sequence encoding the small peptide; a nucleic acid sequence encoding at least 1, 2, 3, 4, 5, 6, 8, 10 amino acid residues but preferably not more than 30 to 50 residues. In a preferred embodiment, the nucleic acid sequence encodes a multibasic cleavage site having the amino acid sequence Arg-Ala-Arg-Ala-Arg-Arg (SEQ ID NO:1). In another preferred embodiment, the nucleic acid sequence encodes a cleavage site having the amino acid sequence X-Arg-X-X-Arg. In a preferred embodiment, the site is cleaved such that the small peptide does not include any extraneous sequence. In another preferred embodiment, the site is cleaved such that the small peptide includes less than 10, 5, 4, 3, 2, or 1 extraneous amino acid residues.

In another preferred embodiment, the product, e.g., a small peptide, is produced as a fusion peptide, e.g., a fusion peptide which includes a pro-region of somatostatin or a functional fragment thereof and a small peptide.

In a preferred embodiment, when the small peptide is produced as a fusion peptide, there is a site between the pro-region and the sequence encoding the small peptide. The site can be a nucleic acid encoding at least 1, 2, 3, 4, 5, 6, 8, 10 amino acids but preferably not more than 30 to 50 amino acids. In a preferred embodiment, the site can be: a nucleic acid sequence encoding amino acids which are not cleaved, e.g., the site is not recognized by an enzyme capable of cleaving the site; a nucleic acid encoding a site capable of being cleaved, e.g., a site which is recognized and cleaved by an enzyme; a nucleic acid encoding an altered site which is recognized and cleaved by an enzyme but is cleaved less efficiently than the site normally recognized by the enzyme.

In a preferred embodiment, when the small peptide is produced as a fusion peptide having a site which is not capable of being cleaved, the site includes at least 1, 2, 3, 4, 5, 6, 8, 10 amino acids but preferably not more than 30 to 50 amino acids which are not recognized as a cleavage site by an enzyme, e.g., an endoprotease. For example, a site which is not capable of being cleaved can be a series of alanine residues, e.g., at least 1, 2, 3, 4, 5, 6, 8, or 10 alanine residues.

In a preferred embodiment, when the small peptide is produced as a fusion peptide having a site which is capable of being cleaved, the site can include at least 1, 2, 3, 4, 5, 6, 8, 10 but preferably not more than 30 to 50 amino acids which are recognized as a cleavage site by an enzyme. A site capable of being cleaved can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, an enzyme which is preferentially expressed in a tissue or fluid recognizes the site capable of being cleaved. For example, the enzyme can be an enzyme preferentially expressed in blood. An example of a site recognized by an enzyme preferentially expressed in blood is a blood coagulation cleavage site, e.g., a blood coagulation factor Xa cleavage site, e.g., a site having the amino acid sequence $X_1$-$X_2$-Gly-Arg, wherein $X_1$ is Iso, Leu, Pro or Ala and $X_2$ is a Gly, Asp, Gln or Asn residue. Other blood coagulation cleavage sites are described, for example, in U.S. Pat. No. 6,010,883, the contents of which is incorporated herein by reference.

In preferred embodiment, when the small peptide is produced as a fusion peptide, the fusion peptide includes an altered site which is recognized and cleaved by an enzyme but is cleaved less efficiently than the site normally recognized by the enzyme. For example, the site can be a cleavage site which is recognized by an enzyme, e.g., an endoprotease, but which has been modified such that the enzyme cleaves the site less efficiently than the unmodified cleavage site. The site can be modified such that at least 1, 2, 3, 4, 5, 6, 8, or 10 amino acids are substituted, deleted or added to the cleavage site. For example, a site having 1, 2, or 3 arginine(s) is less efficiently recognized by the endoprotease furin than a site having 4 or more arginine residues.

In a preferred embodiment, when the small peptide is produced as a fusion peptide having a site capable of cleavage (e.g., a site which is cleaved by an enzyme or an altered site which is recognized by an enzyme but cleaved less efficiently than an unaltered site), the site is: part of the pro-region of a somatostatin nucleic acid sequence; part of the nucleic acid sequence of the small peptide; formed at the junction of the pro-region and the sequence encoding the small peptide; the site is cleaved such that the small peptide does not include any extraneous sequence; the site is cleaved such that the small peptide includes less than 10, 5, 4, 3, 2, or 1 extraneous amino acid residues.

In another preferred embodiment, the small peptide is produced as a fusion peptide and there are no additional amino acids present between the pro-region and the small peptide.

In a preferred embodiment, the nucleic acid sequence encodes: the pro-region of human somatostatin or a functional fragment or sequence variant thereof; the pre-region of human somatostatin or a functional fragment thereof; the prepro-region of human somatostatin or a functional fragment or sequence variant thereof. In a preferred embodiment, the pre-, pro-, or prepro-region differs from wild-type by 1 but not more than 5, 10, 12, 25, 27, 30, 35, 40, 44, 48, 50 amino acid residues.

In a preferred embodiment, the small peptide is a human small peptide, e.g., a human small hormone, e.g., a human anti-diabetogenic peptide, e.g., human GLP-1, e.g., GLP-1 (7-37), GLP-1 (7-36), or a fragment variant thereof. In a preferred embodiment, the nucleic acid sequence encoding a small peptide is a synthetic nucleic acid, e.g., a synthetic nucleic acid which encodes a small peptide wherein at least one non-common or less common codon of the peptide has been replaced by a common codon.

In another aspect, the invention features a method of providing a product, e.g., a small peptide, to a subject. In a preferred embodiment, the product is provided to treat a subject, e.g., a subject having a disorder characterized by a deficiency in a product, e.g., a small peptide.

In one embodiment, the method includes: administering to the subject a cell, e.g., a mammalian cell, which includes an exogenous nucleic acid sequence which includes a nucleic acid sequence encoding a signal peptide, a nucleic acid sequence which encodes the pro-region of a somatostatin or a functional fragment or variant thereof, and a nucleic acid sequence, e.g., a cDNA genomic sequence encoding a product, e.g., a small peptide, to thereby express the product in the subject. In a preferred embodiment, the exogenous nucleic acid sequence is integrated into the genome of the cell. In another preferred embodiment, the exogenous nucleic acid sequence is carried on an extra chromosomal element, e.g., plasmids, episomes, cosmids, phagemids and artificial chromosomes.

In another embodiment, the method includes: administering to a subject a cell, e.g., a mammalian cell having integrated into its genome an exogenous nucleic acid sequence which includes a nucleic acid sequence which encodes the pro-region of a somatostatin or a functional fragment or variant thereof. The cell can be one which does not normally make or contain the product, e.g., the small peptide, or can be one which normally makes or contains the product, e.g., the small peptide. For example, the cell can be a cell which makes or contains the product but in lower quantities than normal (e.g., in quantities less than the physiologically normal levels) or in a defective form or a cell which makes the product at physiologically normal levels, but is augmented to enhance the content or production of a small peptide. The genome of the cell is modified by operatively linking the exogenous nucleic acid sequence to a nucleic acid sequence within the genome of the cell which encodes a product, e.g., a small peptide. In a preferred embodiment, the exogenous nucleic acid further encodes a signal peptide.

In a preferred embodiment, the disorder is a disorder characterized by decreased expression of a product, e.g., a small peptide.

In a preferred embodiment, the subject is human.

In a preferred embodiment, the cell is: a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells; a transformed or immortalized cell line; a cell other than an endocrine cell; one in which somatostatin is not normally expressed. Preferably, the cell is a human cell.

In a preferred embodiment, the sequence encoding the signal peptide is from the pre-region of a somatostatin.

In a preferred embodiment, the product is a small peptide. In a preferred embodiment, the small peptide is: a small hormone; an anti-diabetogenic peptide, e.g., an anti-diabetogenic peptide selected from the group consisting of glucagon-like peptide-1 (GLP-1), e.g., GLP-1 (7-37), GLP-1 (7-36), insulin, insulin-like growth factor-1, insulin-like growth factor-2, exendin4, gastric inhibitory polypeptide and analogs thereof. In a preferred embodiment, the analog of GLP-1 is GLP-1-Gly8.

In a preferred embodiment, the small peptide is an anti-diabetogenic peptide and the subject has diabetes.

In a preferred embodiment, the small peptide is produced in mature form, e.g., the pro-region of somatostatin is cleaved from the small peptide. In a preferred embodiment, there is a site between the pro-region and the sequence encoding the small peptide at which the small peptide can be cleaved from a precursor. The exogenous nucleic acid sequence can include a sequence encoding the cleavage site. For example, the exogenous sequence can encode a pro-region of somatostatin or a functional fragment thereof, a sequence encoding the small peptide, and a site between the pro-region and the sequence encoding the small peptide. In another embodiment, the exogenous nucleic acid sequence can introduce a site of cleavage. The integration of the exogenous sequence can give rise to a site between the pro-region and the sequence encoding the small peptide at which the small peptide can be cleaved from a precursor. The site can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, or PC6. In a preferred embodiment, the site is: part of the pro-region of a somatostatin nucleic acid sequence; part of the nucleic acid sequence of the product, e.g., the small peptide; formed at the junction of the pro-region and the sequence encoding the product; a nucleic acid sequence encoding at least 1, 2, 3, 4, 5, 6, 8, 10 amino acid residues but preferably not more than 30 to 50 residues. In a preferred embodiment, the nucleic acid sequence encodes a multibasic cleavage site having the amino acid sequence Arg-Ala-Arg-Ala-Arg-Arg (SEQ ID NO:1). In another preferred embodiment, the nucleic acid sequence encodes a cleavage site having the amino acid sequence X-Arg-X-X-Arg. In a preferred embodiment, the site is cleaved such that the product does not include any extraneous sequence. In a preferred embodiment, the site is cleaved such that the product includes less than 10, 5, 4, 3, 2, or 1 extraneous amino acid residue.

In another preferred embodiment, the small peptide is produced as a fusion peptide, e.g., a fusion peptide which includes a pro-region of somatostatin or a functional fragment thereof and a small peptide.

In a preferred embodiment, when the small peptide is produced as a fusion peptide, there is a site between the pro-region and the sequence encoding the small peptide. The site can be a nucleic acid encoding at least 1, 2, 3, 4, 5, 6, 8, 10 amino acids but preferably not more than 30 to 50 amino acids. In a preferred embodiment, the site can be: a nucleic acid sequence encoding amino acids which are not cleaved, e.g., the site is not recognized by an enzyme capable of cleaving the site; a nucleic acid encoding a site capable of being cleaved, e.g., a site which is recognized and cleaved by an enzyme; a nucleic acid encoding an altered site which is recognized and cleaved by an enzyme but is cleaved less efficiently than the site normally recognized by the enzyme.

In a preferred embodiment, when the small peptide is produced as a fusion peptide having a site which is not capable of being cleaved, the site includes at least 1, 2, 3, 4, 5, 6, 8, 10 amino acids but preferably not more than 30 to 50 amino acids which are not recognized as a cleavage site by an enzyme, e.g., an endoprotease. For example, a site which is not capable of being cleaved can be a series of alanine residues, e.g., at least 1, 2, 3, 4, 5, 6, 8, or 10 alanine residues.

In a preferred embodiment, when the small peptide is produced as a fusion peptide having a site which is capable of being cleaved, the site can include at least 1, 2, 3, 4, 5, 6, 8, 10 but preferably not more than 30 to 50 amino acids which are recognized as a cleavage site by an enzyme. A site capable of being cleaved can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, an enzyme which is preferentially expressed in a tissue or fluid recognizes the site capable of being cleaved. For example, the enzyme can be an enzyme preferentially expressed in blood. An example of a site recognized by an enzyme preferentially expressed in blood is a blood coagulation cleavage site, e.g., a blood coagulation factor Xa cleavage site, e.g., a site having the amino acid sequence $X_1$-$X_2$-Gly-Arg, wherein $X_1$ is Iso, Leu, Pro or Ala and $X_2$ is a Gly, Asp, Gln or Asn residue. Other blood coagulation cleavage sites are described, for example, in U.S. Pat. No. 6,010,883, the contents of which is incorporated herein by reference.

In preferred embodiments, when the small peptide is produced as a fusion peptide, the fusion peptide includes an altered site which is recognized and cleaved by an enzyme but is cleaved less efficiently than the site normally recognized by the enzyme. For example, the site can be a cleavage site which is recognized by an enzyme, e.g., an endoprotease, but which has been modified such that the enzyme cleaves the site less efficiently than the unmodified cleavage site. The site can be modified such that at least 1, 2, 3, 4, 5, 6, 8, or 10 amino acids are substituted, deleted or added to the cleavage site. For example, a site having 1, 2, or 3 arginine(s) is less efficiently recognized by the endoprotease furin than a site having 4 or more arginine residues.

In a preferred embodiment, when the small peptide is produced as a fusion peptide having a site capable of cleavage (e.g., a site which is cleaved by an enzyme or an altered site which is recognized by an enzyme but cleaved less efficiently than an unaltered site), the site is: part of the pro-region of a somatostatin nucleic acid sequence; part of the nucleic acid sequence of the small peptide; formed at the junction of the pro-region and the sequence encoding the small peptide; the site is cleaved such that the small peptide does not include any extraneous sequence; the site is cleaved such that the small peptide includes less than 10, 5, 4, 3, 2, or 1 extraneous amino acid residues.

In another preferred embodiment, the small peptide is produced as a fusion peptide and there are no additional amino acids present between the pro-region and the small peptide.

In a preferred embodiment, the nucleic acid sequence encodes: the pro-region of human somatostatin or a functional fragment or sequence variant thereof; the pre-region of human somatostatin or a functional fragment thereof; the prepro-region of human somatostatin or a functional fragment or sequence variant thereof. In a preferred embodiment, the pre-, pro-, or prepro-region differs from wild-type by 1 but not more than 5, 10, 12, 25, 27, 30, 35, 40, 44, 48, 50 amino acid residues.

In a preferred embodiment, the small peptide is a human small peptide, e.g., a human small hormone, e.g., a human anti-diabetogenic peptide, e.g., human GLP-1 or a fragment or variant thereof. In a preferred embodiment, the product is a human protein or a functional fragment or variant thereof. In a preferred embodiment, the protein is: a secreted protein, e.g., a hormone, a growth factor, a neurotrophic factor, a binding protein, a cytokine, an angiogenic or antiangiogenic protein, a blood cell regulator. In a preferred embodiment, the protein is: leptin, calcitonin, growth hormone, agouti, agouti signaling protein, agouti-related protein, myostatin, fibroblast growth factor, epidermal growth factor, keratinocyte growth factor, transforming growth factor, hepatocyte growth factor, bone morphogenetic protein, nerve growth factor, neurotrophin, glial-derived neurotrophic factor, brain-derived neurotrophic factor, insulin-like growth factor binding protein, acid-labile subunit, tumor necrosis factor alpha, interleukins, interferons, vascular endothelial growth factor, angiostatin, endostatin, platelet-derived growth factor, granulocyte colony stimulating factor, erythropoeitin. In a preferred embodiment, the nucleic acid sequence encoding a small peptide is a synthetic nucleic acid, e.g., a synthetic nucleic acid which encodes a small peptide wherein at least one non-common or less common codon of the peptide has been replaced by a common codon.

In a preferred embodiment, the cell is: an autologous cell; an allogenic cell; a xenogeneic cell.

In another aspect, the invention features a method of using a genetically engineered cell, e.g., a cell described herein, to provide a product, e.g., a small peptide.

In one embodiment, the method includes: obtaining a cell from a recipient subject; introducing into the cell a nucleic acid construct, e.g., a construct described herein, which includes a nucleic acid sequence encoding a signal peptide, a nucleic acid sequence which encodes the pro-region of a somatostatin or a functional fragment or variant thereof, and a nucleic acid sequence, e.g., a cDNA genomic sequence, encoding a product, e.g., a small peptide; and administering the genetically engineered cell into the recipient subject, to thereby produce the product, e.g., the small peptide, in the subject.

In another embodiment, the method includes: obtaining a cell from a recipient subject; introducing into the cell an exogenous nucleic acid sequence which encodes the pro-region of a somatostatin or a functional fragment or variant thereof; administering the genetically engineered cell into the recipient subject. The cell can be one which does not normally make or contain the product, e.g., the small peptide, or can be one which normally makes or contains the product, e.g., the small peptide. For example, the cell can be a cell which makes or contains the product but in lower quantities than normal (e.g., in quantities less than the physiologically normal levels) or in a defective form or a cell which makes the product, e.g., the small peptide at physiologically normal levels, but is augmented to enhance the content or production of a small peptide. The genome of the cell is modified by operatively linking the exogenous nucleic acid sequence to a nucleic acid sequence within the genome of the cell which encodes a product. The exogenous nucleic acid sequence can introduce a site for cleavage. In a preferred embodiment, the exogenous nucleic acid sequence further encodes a signal peptide.

In a preferred embodiment, the subject is a human.

In a preferred embodiment, the cell is: a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells; a transformed or immortalized cell line; a cell other than an endocrine cell; one in which somatostatin is not normally expressed. Preferably, the cell is a human cell.

In a preferred embodiment, the cell further includes at least one regulatory sequence, sufficient for expression of the exogenous nucleic acid sequence in the cell. In a preferred embodiment, the regulatory sequence is a 5' regulatory sequence, e.g., a 5' flanking sequence (e.g., a promoter and/or an enhancer), and/or 5' untranslated region (5'UTR); a 3' regulatory sequence, e.g., a 3' untranslated region (3'UTR) (e.g., a polyadenylation sequence) and/or a 3' flanking sequence; at least one splice junction site. The regulatory sequence can be a viral or a non-viral sequence. In a preferred embodiment, the regulatory sequence can be: the regulatory sequence that normally occurs with the product, e.g., the small peptide, the regulatory sequence of CMV, elastase, aldolase, or other constitutively active regulatory sequences; a glucose-responsive regulatory sequence, e.g., an insulin regulatory sequence; a regulatory sequence involved in feeding/satiety behavior, e.g., a leptin regulatory sequence.

In a preferred embodiment, the sequence encoding the signal peptide is from the pre-region of a somatostatin.

In a preferred embodiment, the small peptide is: a small hormone; an anti-diabetogenic peptide, e.g., an anti-diabetic peptide is selected from the group consisting of glucagon-like peptide-1 (GLP-1), e.g., GLP-1 (7-37), GLP-1 (7-36), insulin, insulin-like growth factor-1, insulin growth factor-2, exendin-4, gastric inhibitory polypeptide and analogs thereof. In a preferred embodiment, the analog of GLP-1 is GLP-1-Gly8.

In a preferred embodiment, the product, e.g., a small peptide, is produced in mature form, e.g., the pro-region of somatostatin is cleaved from the small peptide. In a preferred embodiment, there is a site between the pro-region and the sequence encoding the small peptide at which the small peptide can be cleaved from a precursor. The exogenous nucleic acid sequence can include a sequence encoding the cleavage site. For example, the exogenous sequence can encode a pro-region of somatostatin or a functional fragment thereof, a sequence encoding the small peptide, and a site between the pro-region and the sequence encoding the small peptide. In another embodiment, the exogenous nucleic acid sequence can introduce a site of cleavage. The integration of the exogenous sequence can give rise to a site between the pro-region and the sequence encoding the small peptide at which the small peptide can be cleaved from a precursor. The site can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, the site is: part of the pro-region of a somatostatin nucleic acid sequence; part of the nucleic acid sequence of the product, e.g., the small peptide; formed at the junction of the pro-region and the sequence encoding the product; a nucleic acid sequence encoding at least 1, 2, 3, 4, 5, 6, 8, 10 amino acid residues but preferably not more than 30 to 50 amino acid residues. In a preferred embodiment, the nucleic acid sequence encodes a multibasic cleavage site having the amino acid sequence Arg-Ala-Arg-Ala-Arg-Arg (SEQ ID NO:1). In another preferred embodiment, the nucleic acid sequence encodes a cleavage site having the amino acid sequence X-Arg-X-X-Arg. In a preferred embodiment, the site is cleaved such that the product does not include any extraneous sequence. In another preferred embodiment, the site is cleaved such that the product includes less than 10, 5, 4, 3, 2, or 1 extraneous amino acid residue.

In another preferred embodiment, the product, e.g., the small peptide, is produced as a fusion peptide, e.g., a fusion peptide which includes a pro-region of somatostatin or a functional fragment thereof and a small peptide.

In a preferred embodiment, when the small peptide is produced as a fusion peptide, there is a site between the pro-region and the sequence encoding the small peptide. The site can be a nucleic acid encoding at least 1, 2, 3, 4, 5, 6, 8, 10 amino acids but preferably not more than 30 to 50 amino acids. In a preferred embodiment, the site can be: a nucleic acid sequence encoding amino acids which are not cleaved, e.g., the site is not recognized by an enzyme capable of cleaving the site; a nucleic acid encoding a site capable of being cleaved, e.g., a site which is recognized and cleaved by an enzyme; a nucleic acid encoding an altered site which is recognized and cleaved by an enzyme but is cleaved less efficiently than the site normally recognized by the enzyme.

In a preferred embodiment, when the small peptide is produced as a fusion peptide having a site which is not capable of being cleaved, the site includes at least 1, 2, 3, 4, 5, 6, 8, 10 amino acids but preferably not more than 30 to 50 amino acids which are not recognized as a cleavage site by an enzyme, e.g., an endoprotease. For example, a site which is not capable of being cleaved can be a series of alanine residues, e.g., at least 1, 2, 3, 4, 5, 6, 8, or 10 alanine residues.

In a preferred embodiment, when the small peptide is produced as a fusion peptide having a site which is capable of being cleaved, the site can include at least 1, 2, 3, 4, 5, 6, 8, 10 but preferably not more than 30 to 50 amino acids which are recognized as a cleavage site by an enzyme. A site capable of being cleaved can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, an enzyme which is preferentially expressed in a tissue or fluid recognizes the site capable of being cleaved. For example, the enzyme can be an enzyme preferentially expressed in blood. An example of a site recognized by an enzyme preferentially expressed in blood is a blood coagulation cleavage site, e.g., a blood coagulation factor Xa cleavage site, e.g., a site having the amino acid sequence $X_1$-$X_2$-Gly-Arg, wherein $X_1$ is Iso, Leu, Pro or Ala and $X_2$ is a Gly, Asp, Gln or Asn residue. Other blood coagulation cleavage sites are described, for example, in U.S. Pat. No. 6,010,883, the contents of which is incorporated herein by reference.

In preferred embodiment, when the small peptide is produced as a fusion peptide, the fusion peptide includes an altered site which is recognized and cleaved by an enzyme but is cleaved less efficiently than the site normally recognized by the enzyme. For example, the site can be a cleavage site which is recognized by an enzyme, e.g., an endoprotease, but which has been modified such that the enzyme cleaves the site less efficiently than the unmodified cleavage site. The site can be modified such that at least 1, 2, 3, 4, 5, 6, 8, or 10 amino acids are substituted, deleted or added to the cleavage site. For example, a site having 1, 2, or 3 arginine(s) is less efficiently recognized by the endoprotease furin than a site having 4 or more arginine residues.

In a preferred embodiment, when the small peptide is produced as a fusion peptide having a site capable of cleavage (e.g., a site which is cleaved by an enzyme or an altered site which is recognized by an enzyme but cleaved less efficiently than an unaltered site), the site is: part of the pro-region of a somatostatin nucleic acid sequence; part of the nucleic acid sequence of the small peptide; formed at the junction of the pro-region and the sequence encoding the small peptide; the site is cleaved such that the small peptide does not include any extraneous sequence; the site is cleaved such that the small peptide includes less than 10, 5, 4, 3, 2, or 1 extraneous amino acid residues.

In another preferred embodiment, the small peptide is produced as a fusion peptide and there are no additional amino acids present between the pro-region and the small peptide.

In a preferred embodiment, the subject is a human subject. In a preferred embodiment, the subject has: a disorder characterized by a deficiency of a product, e.g., a small peptide, e.g., a disorder characterized by decreased expression of a product, e.g., decreased expression of a small peptide. In another preferred embodiment, the subject has diabetes.

In a preferred embodiment, the nucleic acid sequence encodes: the pro-region of human somatostatin or a functional fragment or analog thereof, the pre-region of human somatostatin or a functional fragment thereof; the preproregion of human somatostatin or a functional fragment or analog thereof. In a preferred embodiment, the pre-, pro-, or prepro-region differs from wild-type by 1 but not more than 5, 10, 12, 25, 27, 30, 35, 40, 44, 48, 50 amino acid residues.

In a preferred embodiment, the product is a small peptide. In a preferred embodiment, the small peptide is a human small peptide, e.g., a human small hormone, e.g., a human anti-diabetogenic peptide, e.g., human GLP-1 or a fragment or analog thereof. In a preferred embodiment, the nucleic acid sequence encoding a product is a synthetic nucleic acid, e.g., a synthetic nucleic acid which encodes a product wherein at least one non-common or less common codon of the product has been replaced by a common codon.

In another aspect, the invention features a method of providing an anti-diabetogenic peptide to a subject, e.g., a subject having diabetes.

In one embodiment, the method includes: administering to a subject a cell, e.g., a cell described herein, which includes an exogenous nucleic acid sequence which includes a nucleic acid sequence encoding a signal peptide, a nucleic acid sequence which encodes the pro-region of a somatostatin or a functional fragment or variant thereof, and a nucleic acid sequence encoding an anti-diabetogenic peptide, e.g., a cDNA or genomic sequence, to thereby express the anti-diabetogenic peptide in the subject. In a preferred embodiment, the exogenous nucleic acid sequence is integrated into the genome of the cell. In another preferred embodiment, the exogenous nucleic acid sequence is carried on an extra chromosomal element, e.g., plasmids, episomes, cosmids, phagemids and artificial chromosomes.

In another embodiment, the method includes: administering to a subject a cell having integrated into its genome an exogenous nucleic acid sequence which includes a nucleic acid sequence which encodes the pro-region of a somatostatin or a functional fragment or variant thereof. The cell can be one which does not normally make or contain the anti-diabetogenic peptide or can be one which normally makes or contains the small peptide. For example, the cell can be a cell which makes or contains the small peptide but in lower quantities than normal (e.g., in quantities less than the physiologically normal levels) or in a defective form or a cell which makes the small peptide at physiologically normal levels, but is augmented to enhance the content or production of a small peptide. The genome of the cell is modified by operatively linking the exogenous nucleic acid sequence to a nucleic acid sequence within the genome of the cell which encodes a small peptide. In a preferred embodiment, the exogenous nucleic acid sequence further encodes a signal peptide.

In a preferred embodiment, the subject is a human.

In a preferred embodiment, the sequence encoding the signal peptide is from the pre-region of a somatostatin.

In a preferred embodiment, the cell further includes at least one regulatory sequence, sufficient for expression of the exogenous nucleic acid sequence in the cell. In a preferred embodiment, the regulatory sequence is a 5' regulatory sequence, e.g., a 5' flanking sequence (e.g., a promoter and/or an enhancer), and/or 5' untranslated region (5'UTR); a 3' regulatory sequence, e.g., a 3' untranslated region (3'UTR) (e.g., a polyadenylation sequence) and/or a 3' flanking sequence; at least one splice junction site. The regulatory sequence can be a viral or a non-viral sequence. In a preferred embodiment, the regulatory sequence can be: the regulatory sequence that normally occurs with the product, e.g., the small peptide, the regulatory sequence of CMV, elastase, aldolase, or other constitutively active regulatory sequences; a glucose-responsive regulatory sequence, e.g., an insulin regulatory sequence; a regulatory sequence involved in feeding/satiety behavior, e.g., a leptin regulatory sequence.

In a preferred embodiment, the anti-diabetogenic peptide is an anti-diabetogenic selected from the group consisting of glucagon-like peptide-1 (GLP-1), e.g., GLP-1 (7-37), GLP-1 (7-36), exendin-4, gastric inhibitory polypeptide and analogs thereof. In a preferred embodiment, the analog of GLP-1 is GLP-1-Gly8.

In a preferred embodiment, the anti-diabetogenic peptide can be produced in mature form, e.g., the pro-region of somatostatin is cleaved from the anti-diabetogenic peptide. In a preferred embodiment, there is a site between the pro-region and the sequence encoding the anti-diabetogenic peptide at which the anti-diabetogenic peptide can be cleaved from a precursor. The exogenous nucleic acid sequence can include a sequence encoding the cleavage site. For example, the exogenous sequence can encode a pro-region of somatostatin or a functional fragment thereof, a sequence encoding the anti-diabetogenic peptide, and a site between the pro-region and the sequence encoding the anti-diabetogenic peptide. In another embodiment, the exogenous nucleic acid sequence can introduce a site of cleavage. The integration of the exogenous sequence can give rise to a site between the pro-region and the sequence encoding the anti-diabetogenic peptide at which the anti-diabetogenic peptide can be cleaved from a precursor. The site can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, substilisin-related pro-protein convertase, PC1, or PC12. In a preferred embodiment, the site is: part of the pro-region of a somatostatin nucleic acid sequence; part of the nucleic acid sequence of the small peptide; formed at the junction of the pro-region and the sequence encoding the small peptide; a nucleic acid sequence encoding at least 1, 2, 3, 4, 5, 6, 8, 10 amino acid residues but preferably not more than 30 to 50 residues. In a preferred embodiment, the nucleic acid sequence encodes a multibasic cleavage site having the amino acid sequence Arg-Ala-Arg-Ala-Arg-Arg (SEQ ID NO:1). In another preferred embodiment, the nucleic acid sequence encodes a cleavage site having the amino acid sequence X-Arg-X-X-Arg. In a preferred embodiment, the site is cleaved such that the small peptide does not include any extraneous sequence. In another preferred embodiment, the site is cleaved such that the small peptide includes less than 10, 5, 4, 3, 2, or 1 extraneous amino acid residues.

In another preferred embodiment, the anti-diabetogenic peptide, is produced as a fusion peptide, e.g., a fusion peptide which includes a pro-region of somatostatin or a functional fragment thereof and an anti-diabetogenic peptide.

In a preferred embodiment, when the anti-diabetogenic peptide is produced as a fusion peptide, there is a site between the pro-region and the sequence encoding the anti-diabetogenic peptide. The site can be a nucleic acid encoding at least 1, 2, 3, 4, 5, 6, 8, 10 amino acids but preferably not more than 30 to 50 amino acids. In a preferred embodiment, the site can be: a nucleic acid sequence encoding amino acids which are not cleaved, e.g., the site is not recognized by an enzyme capable of cleaving the site; a nucleic acid encoding a site capable of being cleaved, e.g., a site which is recognized and cleaved by an enzyme; a nucleic acid encoding an altered site which is recognized and cleaved by an enzyme but is cleaved less efficiently than the site normally recognized by the enzyme.

In a preferred embodiment, when the anti-diabetogenic peptide is produced as a fusion peptide having a site which is not capable of being cleaved, the site includes at least 1, 2, 3, 4, 5, 6, 8, 10 amino acids but preferably not more than 30 to 50 amino acids which are not recognized as a cleavage site by an enzyme, e.g., an endoprotease. For example, a site which is not capable of being cleaved can be a series of alanine residues, e.g., at least 1, 2, 3, 4, 5, 6, 8, or 10 alanine residues.

In a preferred embodiment, when the anti-diabetogenic peptide is produced as a fusion peptide having a site which is capable of being cleaved, the site can include at least 1, 2, 3, 4, 5, 6, 8, 10 but preferably not more than 30 to 50 amino acids which are recognized as a cleavage site by an enzyme. A site capable of being cleaved can be: a nucleic acid sequence encoding a multibasic, dibasic or monobasic cleavage site; a nucleic acid sequence encoding an endoprotease cleavage site; a nucleic acid sequence encoding a cleavage site recognized by a pro-protein convertase, e.g., furin, PACE4, substilisin-related pro-protein convertase, PC1, PC2, PC6 or PC7. In a preferred embodiment, an enzyme which is preferentially expressed in a tissue or fluid recognizes the site capable of being cleaved. For example, the enzyme can be an enzyme preferentially expressed in blood. An example of a site recognized by an enzyme preferentially expressed in blood is a blood coagulation cleavage site, e.g., a blood coagulation factor Xa cleavage site, e.g., a site having the amino acid sequence $X_1$-$X_2$-Gly-Arg, wherein $X_1$ is Iso, Leu, Pro or Ala and $X_2$ is a Gly, Asp, Gln or Asn residue. Other blood coagulation cleavage sites are described, for example, in U.S. Pat. No. 6,010,883, the contents of which is incorporated herein by reference.

In preferred embodiment, when the anti-diabetogenic peptide is produced as a fusion peptide, the fusion peptide includes an altered site which is recognized and cleaved by an enzyme but is cleaved less efficiently than the site normally recognized by the enzyme. For example, the site can be a cleavage site which is recognized by an enzyme, e.g., an endoprotease, but which has been modified such that the enzyme cleaves the site less efficiently than the unmodified cleavage site. The site can be modified such that at least 1, 2, 3, 4, 5, 6, 8, or 10 amino acids are substituted, deleted or added to the cleavage site. For example, a site having 1, 2, or 3 arginine(s) is less efficiently recognized by the endoprotease furin than a site having 4 or more arginine residues.

In a preferred embodiment, when the anti-diabetogenic peptide is produced as a fusion peptide having a site capable of cleavage (e.g., a site which is cleaved by an enzyme or an altered site which is recognized by an enzyme but cleaved less efficiently than an unaltered site), the site is: part of the pro-region of a somatostatin nucleic acid sequence; part of the nucleic acid sequence of the anti-diabetogenic peptide; formed at the junction of the pro-region and the sequence encoding the anti-diabetogenic peptide; the site is cleaved such that the anti-diabetogenic peptide does not include any extraneous sequence; the site is cleaved such that the anti-diabetogenic peptide includes less than 10, 5, 4, 3, 2, or 1 extraneous amino acid residues.

In another preferred embodiment, the anti-diabetogenic peptide is produced as a fusion peptide and there are no additional amino acids present between the pro-region and the anti-diabetogenic peptide.

In a preferred embodiment, the nucleic acid sequence encodes: the pro-region of human somatostatin or a functional fragment or sequence variant thereof, the pre-region of human somatostatin or a functional fragment thereof, the prepro-region of human somatostatin or a functional fragment or sequence variant thereof. In a preferred embodiment, the pre-, pro-, or prepro-region differs from wild-type by 1 but not more than 5, 10, 12, 25, 27, 30, 35, 40, 44, 48, 50 amino acid residues.

In a preferred embodiment, the small peptide is a human small peptide, e.g., a human small hormone, e.g., a human anti-diabetogenic peptide, e.g., human GLP-1, e.g., GLP-1 (7-37), GLP-1 (7-36), or a fragment or variant thereof. In a preferred embodiment, the nucleic acid sequence encoding a small peptide is a synthetic nucleic acid, e.g., a synthetic nucleic acid which encodes a small peptide wherein at least one non-common or less common codon of the peptide has been replaced by a common codon.

In a preferred embodiment, the cell is a human cell. In a preferred embodiment, the cell is: a mammalian cell, e.g., a primary or secondary mammalian cell, e.g., a fibroblast, a hematopoietic stem cell, a myoblast, a keratinocyte, an epithelial cell, an endothelial cell, a glial cell, a neural cell, a cell comprising a formed element of the blood, a muscle cell and precursors of these somatic cells; an autologous cell; an allogeneic cell; an xenogeneic cell; a cell other than an endocrine cell; one which does not normally express somatostatin.

The terms "protein," polypeptide" and "peptide" are used interchangeably herein. A "heterologous" peptide as used herein refers to a peptide other than somatostatin.

Small peptides include any small peptide other than somatostatin. A "small peptide," as used herein, refers to a peptide having 2, 3, 4, or 5 to 70 amino acid residues. In a preferred embodiment, the small peptide is 10 to 60 amino acid residues in length. In other preferred embodiments, it is 20 to 50 amino acid residues in length. Examples of small peptides include hormones (e.g., anti-diabetogenic peptides), and/or including enkephalins, GLP-1 (e.g., GLP-1 (7-37), GLP-1 (7-36)), GLP-2, insulin, insulin-like growth factor-1, insulin-like growth factor-2, orexin A, orexin B, neuropeptide Y, growth hormone-releasing hormone, thryotropin-releasing hormone, cholecystokinin, melanocyte-stimulating hormone, corticotrophin-releasing factor, melanin concentrating hormone, galanin, bombesin, calcitonin gene related peptide, neurotensin, endorphin, dynorpin, the C-peptide of proinsulin. The phrase "an active form" of a peptide or protein refers to a peptide or protein in which the signal peptide and/or pro-region has been removed, e.g., cleaved.

The term "preferentially expressed" in a tissue or fluid, as used herein, refers to a polypeptide, e.g., an enzyme, which is expressed at higher levels in the tissue or cell chosen than in other tissues or cells. The protein can be substantially produced only in that tissue or cell or can be found to be present in higher levels in that tissue or fluid than the levels found in other tissues or fluids. For example, the protein, e.g., enzyme, can be detected at higher levels in blood than in other tissues.

The term "cleaved less efficiently" refers to a site at which the rate at which an enzyme is capable of cleaving the site is less than the rate at which the enzyme cleaves a site naturally recognized by that enzyme. For example, the enzyme furin recognizes and provides cleaves a site having four or more arginine residues more rapidly and/or with a greater number of sites being cleaved than a site having 1, 2, or 3 arginine residues.

It has been found that signal peptide/pro-region somatostatin/peptide fusions provide several advantages. For example, a number of pro-regions from other precursors were used to replace the somatostatin pro-region and it was found that other pro-regions do not have the ability to direct biosynthesis and secretion of small peptides in this context. The signal sequence and pro-region direct entry into and transport throughout the secretory pathway. The addition of a signal sequence and pro-region to a small peptide such as an enkephalin or small hormone may also allow the peptide to be more efficiently synthesized by ribosomes than the peptide by itself. It was also found that pro-region somatostatin/peptide fusions reduce degradation of small peptides such as GLP-1, thereby increasing the half-life of these peptides in vitro and in vivo.

Other features and advantages of the invention will be apparent from the following description and from the claims.

BRIEF DESCRIPTION OF THE DRAWINGS

FIG. 3 depicts the DNA sequence of the prepro-somatostatin/GLP-1 coding sequence (SEQ ID NO:2) of pXIT-39. Restriction enzyme sites flanking the coding sequence are underlines and labeled. The prepro somatostatin sequence is shown in lower case, with the initiator methionine in bold. The multibasic cleavage site is indicated in upper case bold. The sequence of GLP-1 is in upper case plain text. The translation termination codon is labeled with an asterisk.

FIG. 4 depicts an alignment of the amino acid sequence of human GLP-1 (7-37), human GLP-1 (7-36) and GLP-1 derived from the human fibroblast cell line F G39-38.

DESCRIPTION OF THE PREFERRED EMBODIMENTS

DNA Constructs

Figure 1:
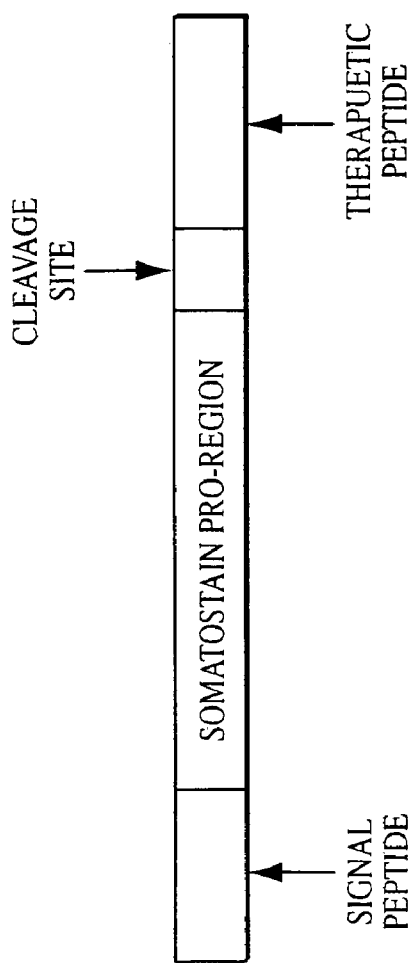
FIG. 1 depicts a schematic representation of a prepro somatostatin/small peptide fusion protein.

DNA constructs, which include a signal sequence, a somatostatin pro-region and a heterologous nucleic acid sequence and, optionally, a nucleic acid sequence encoding a selectable marker, along with additional regulatory sequences sufficient for expression of the heterologous nucleic acid sequence in recipient cells, e.g., primary or secondary cells or cell line, can be used to transfect cells in which a product is to be produced. Alternatively, infectious vectors, can be used for this purpose.

A selectable marker and the heterologous nucleic acid can be carried on a single construct or on a separate constructs. A DNA construct which includes the heterologous nucleic acid sequence and additional regulatory sequences, such as sequences necessary for expression of the exogenous nucleic acid sequence, and a DNA construct which includes DNA encoding a selectable marker, along with additional regulatory sequence, and a DNA construct which includes DAN encoding a selectable marker, along with additional regulatory sequences such as a promoter, polyadenylation site and splice junctions, used to confer a selectable phenotype upon transected primary or secondary cells, can be used to transform the cells. The two DNA constructs are co-transfected into primary or secondary cells using methods described herein. Alternatively, one DNA construct which includes an exogenous DNA, selectable marker gene and additional sequences (e.g., those sufficient for expression of the exogenous DNA and for expression the selectable maker gene) can be used.

Selectable Markers

A variety of selectable markers can be incorporated into the cells, e.g., primary or secondary cells or cell line. For example, a selectable marker which confers a selectable phenotype such as drug resistance, nutritional trophy cytotoxic agent or expression of a surface protein, can be use. Selectable marker genes which can be used include neo, gpt, dhfr, ada, pac, hyg and hisd. The selectable phenotype conferred makes it possible to identify and isolate recipient primary, secondary cells or cell line.

Small Peptides

Small peptides include any small peptide other than somatostatin. The small peptide can be one which: 1) requires a pro region for biosynthesis; 2) is secreted; 3) is a biologically active peptide; and/or 4) has a physiological effect on insulin secretion, obesity or an endocrine disorder.

Preferred small peptides are those which are subject to: 1) synthesis as part of a precursor containing one or more peptides that are release by proteolysis processing; 2) may be activated by endoproteolysis and/or exoproteolysis; and/or 3) may require admiration to become fully active.

Preferably, the small peptide is an anti-diabetogenic peptide. An anti-diabetogenic peptide includes peptide having one or more of the following activities: 1) ability to increase insulin secretion; 2) ability to increase insulin biosynthesis; 3) ability to decrease glucagon secretion; 4) ability to delay gastric emptying; 5) reduce hepatic gluconeogenesis; 6) improve insulin sensitivity; 7) improve glucose sensing by the beta cell; 8) enhance glucose disposal; 9) reduce insulin resistance; and 10) promote β cell function or viability. Examples of anti-diabetogenic peptides include glucagon-like peptide-1 (GLP-1), e.g. GLP-1 (7-37, GLP-1 (7-36), exedin-4, and gastric inhibitory polypeptide.

Nucleotide sequence information for some of the genes encoding small peptides listed above are found in U.S. Pat. No. 5,118,666 (GLP-1 (7-34) and GLP-1 (7-35); U.S. Pat. No. 5,120,712 (GLP-1 (7-37)); U.S. Pat. No. 5,424,286 (exendin-4); and Takeda et al. (1987) *Prot. Natl. Acad. Sci. USA* 84 (20):7005–7008. In a preferred embodiment, the nucleic acid sequence encoding a small peptide is a synthetic nucleic acid, e.g., a synthetic nucleic acid which encodes a small peptide wherein at least one non-common or less common codon of the peptide has been replaced by a common codon. In other preferred embodiments, about 10, 20, 30, 40, 50 60, 70, 80, 90% or all of the codons encoding the small peptide have been optimized. Methods of modifying a nucleic acid sequence to encode a common codon are described in U.S. Ser. No. 09/407,605, the contents of which is incorporated herein by reference.

Variants and analogs of some of the small peptides listed above are known. For example, know variants and analogs of GLP-1 include, for example, GLP-1 (7-36), GLN$^9$-GP-1 (7-37), Thr$^{16}$-Lys$^{18}$-GLP-1 (7-37), Lys$^{18}$-GLP-1 (7-37) and Gly$^8$-GLP-1. Derivatives of GLP-1 include, for example, acid addition salts, carboxylate salts, lower alkyl esters, and amides as described in PCT Publication WO 91/11457, the contents of which is incorporated by reference.

Signal Sequence

A signal sequence is a sequence which directs a peptide having such sequence to a lipid bilayer, e.g., the endoplasmic reticulum (ER). In a preferred embodiment, the signal peptide also assists in transferring the peptide across the bilayer, for example across the lipid bilayer of the ER and into the ER for further processing. A signal sequence should be of sufficient size and hydro-phobicity to direct the peptide for cellular processing. It has been shown that signal sequences from higher eukaryotes and signal sequence should be of sufficient size and hydro-phobicity to direct the peptide for cellular processing. It has been shown that signal sequences from higher eukaryotes and signal sequence from prokaryotic organisms are interchangeable. See, e.g., Gierasch et al. (1989) *Biochemistry* 28:923–930. Thus, a signal sequence can be derived from any secreted protein. Preferably, the signal sequence from genes encoding alkaline phosphates, angiogenin, ant thrombin III, any of the blood clotting factors including Factor VIII, Factor IX, and Factor X, erythropoietin, extra cellular super oxide dismutase, globin, glucocerebrosidase, glutamate decarboxylase, human growth factor, human serum albumin, immunoglobulin, insulin, myelin basic protein, proinsulin, prolactin, lactoferrin, lactoglobulin, lysozyme, lactalbumin, tissue plasminogen activator.

Preferably, the nucleic acid sequence encoding the signal sequence is from the pre-region of somatostatin. For example, the nucleic acid encoding the pre-region of human somatostatin. For example, the nucleic acid encoding the pre-region of human somatostatin can be used. The signal sequence of human somatostatin spans from amino acids 1 to 24 of the amino acid sequence of human somatostatin. See Shen et al. (1984) *Science* 224(4645):168–171. Nucleotide sequence information is also available for genes encoding somatostatin from several different species. See Bruneau et al, (1998) *Peptides* 19(10):1749–1758 9sheep somatostatin); Hoefler et al. (1986) *Nature* 288:137–141 (anglerfish); Funckes et al. (1983) *J. boil. Chem.* 258:8781–8787 (rat somatostatin).

In a preferred embodiment, the nucleic acid sequence encoding a signal sequence is a synthetic nucleic acid, e.g., a synthetic nucleic acid which encodes a signal sequence wherein at least one non-common or less common codon of the signal sequence has been replaced by a common codon. In other preferred embodiments, about 10, 20, 30, 40, 50 60, 70, 80, 90% or all of the codons encoding the signal peptide have been optimized. Methods of modifying a nucleic acid sequence to encode a common codon are described in U.S. Ser. No. 09/407,506, the contents of which is incorporated herein by reference.

Candidate signal sequences can be tested by in vitro or in vivo methods. For example, the candidate signal sequence can be tested by in vitro transcription/translation in the presence or absence of pancreatic microsomal membranes. In vitro transcription/translation using a construct containing a candidate signal sequence fused to a protein such as GLP-1 will yield a product that has the molecular weight of the signal sequence and GLP-1. When the same reaction is performed in the presence of pancreatic microsomal membranes, a functional signal peptide will cross the membrane and be removed by signal peptidase. Therefore, the product recovered will correspond to GLP-1 without the signal peptide only if the signal peptide is functional.

Pro-Region of Somatostatin

The pro-region of a somatostatin or functional fragments and variants thereof are used to optimize the production of a product such as a small peptide. The pro-region contains the information to guide a protein through the biosynthetic processes of the cell secretory pathway. Specifically, the pro-region may facilitate one or more of the following activities: 1) translocation into the endoplasmic reticulum; 2) protein folding in the endoplasmic reticulum; 3) transport through various compartments of the secretory pathway; 4) post-translation processing within the secretory pathway; and 5) secretion from a cell.

Nucleotide sequence information is available for genes encoding pro-somatostatin from various species. See Shen et al. (1984) *Science* 224(4645):168–171 (human somatostatin); Bruneau et al. (1998) *Peptides* 19 (101)Z:1749–1758 (sheep somatostatin); Hoefler et al. (1986) *nature* 288; 137–141 (anglerfish); Funckes et al. (1983) *J. Biol. Chem.* 258:8781–8787 (rat somatostatin).

In addition, functional fragments and variants of the pro-region of a somatostatin can be used. In a preferred embodiment, the nucleic acid sequence encoding the pro-region is a synthetic nucleic acid, e.g., a synthetic nucleic acid which encodes a pro-region wherein at least one non-common or less common codon of the pro-region has been replaced by a common codon. In other preferred embodiments, about 10, 20, 30, 40, 50 60, 70, 80, 90% or all of the codons encoding the pro-region have been optimized. Methods of modifying a nucleic acid sequence to encode a common codon are described in U.S. Ser. No. 09/407,506, the contents of which is incorporated herein by reference.

Preferred sequence variants include pro-region (or functional fragments thereof) whose sequence differ from the wild-type sequence by one or more conservative amino acid substitutions or by one or more non-conservative amino acid substitution, deletions, or insertions which do not abolish the functional activity of the pro-region of somatostatin. Conservative substitutions typically include the substitution of one amino acid for another with similar characteristics, e.g., substitutions within the following groups: valine, glycine; glycine, alanine; valine, isoleucine, leucine; asperity acid, glutamic acid; asparagine, glutamine; serine, threonine; lysine, arginine; and phenylalanine, tyrosine. Other conservative substitutions are known. Preferred sequence variants differ from a wild type pro-region by at least one but not more than 5, 10, 15, 25 or 50 residues.

Variants can be produced by several methods known in the art. For example, non-random or directed, mutagenesis techniques can be used to provide specific sequence or mutations in specific regions. These techniques can be used to create variants which include, e.g. deletions, insertions, or substitutions, of residue of the known amino acid sequence of the pro-region of somatostatin.

One can use art to make fragments or variants. These fragments and variants can be tested to determine if they function as a pro-region by introducing the fragment or variant thereof into an expression vector such as those described in Example I and introducing the vector into a cell. Secretion of a peptide or protein from the cell can be used to determine whether the fragment or variant of the pro-region is functional. See, e.g., Example II below.

Assembly of the DNA Sequences

A nucleic acid sequence including a nucleic acid encoding a signal sequence, a nucleic acid encoding the pro-region of somatostatin and a nucleic acid encoding a small heterologous peptide can be assembled by various methods. For example, the entire nucleotide sequence of the signal peptide/pro-region/small peptide fusion protein can be synthesized as a series of overlapping oligonucleotides that are then ligated together. In addition, the nucleic acid sequence for the signal peptide, the pro-region, and the small peptide, may be amplified by PCR from any starting material that contains the target sequences. PCR primers can be designed to incorporate an endoprotease cleavage site between the pro-region of a somatostatin and the sequence encoding the small heterologous peptide. The fragments can then be joined by overlapping PCR. The nucleic sequence may also be assembled by traditional cloning techniques. This method would involve, for example, the isolation of a signal peptide, the pro-region of somatostatin and a small peptide-encoding nucleotide sequence by restriction digest, followed by ligation of the fragments to an oligonucleotide encoding a site, e.g., a cleavage site, e.g., an endoprotease cleavage site.

Genetically Engineered Cells

Primary and secondary cells to be genetically engineered can be obtained from a variety of tissues and include cell types which can be maintained propagated in culture. For example, primary and secondary cells include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells (myoblasts) and precursors of these somatic cell types. Primary cells are preferably obtained from the individual to whom the genetically engineered primary or secondary cells are administered. However, primary cells may be obtained for a donor (other than the recipient) of the same species or another species (e.g., mouse, rat, rabbit, cat, dog, pig, cow, bird, sheep, goat, horse).

The term "primary cell" includes cells present in a suspension of cells isolated from a vertebrate tissue source (prior to their being plated i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells which have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized. A "clonal cell strain" is defined as a cell strain that is derived from a single founder cell. A "heterogenous cell strain" is defined as a cell strain that is derived from two or more founder cells.

Primary of secondary cells of vertebrate, particularly mammalian, origin can be transfected with an exogenous nucleic acid sequence which includes a nucleic acid sequence encoding a signal peptide, a nucleic acid sequence encoding the pro-region of a somatostatin or functional fragment or analog thereof, and a heterologous nucleic acid sequence, e.g., encoding a small heterologous peptide, and produce an encoded products stably and reproducibly in vitro and in vivo, over extended periods of time. In addition, an exogenous nucleic acid sequence which includes a nucleic acid sequence encoding a signal peptide and a nucleic acid sequence encoding the pro-region of a somatostatin can be introduced into a primary or secondary cell by homologous recombination as described, for example, in U.S. Pat. No. 5,641,670 and U.S. Pat. No. 5,733,761, the contents of which are incorporated herein by reference.

The transfected primary or secondary cells may also include DNA encoding a selectable marker which confers a selectable phenotype upon them, facilitating their identification and isolation. Methods for producing transfected primary and secondary cells which stably express exogenous synthetic DNA, clonal cell strains and heterogeneous cell strains of such transfected cells, methods of producing the clonal heterogeneous cell strains, and methods of treating or preventing an abnormal or undesirable condition through the use of populations of transfected primary or secondary cells are part of the present invention.

Transfection of Primary or Secondary Cells of Clonal or Heterogeneous Cell Strains Vertebrate tissue can be obtained by standard methods such a punch biopsy or other surgical methods of obtaining a tissue source of the primary cell type of interest. For example, punch biopsy I sued to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

The resulting primary cell mixture can be transfected directly or it can be cultured first, removed from the culture plate a resuspended before transfection is carries out. Primary cells or secondary cells are combined with exogenous nucleic acid sequence to e.g., stably integrated into their genomes and, optionally, DNA encoding a selectable marker, and treated in order to accomplish transfection. The exogenous nucleic acid sequence and selectable marker-encoding DNA can either be on separate constructs or on a single construct. An appropriate quantity of DNA is used to ensure that at least one stably transfected cell containing and appropriately expressing exogenous DNA is produced. In general, approximately 0.1 to 500 µg of DNA is used.

As used herein, the term "transfection" includes a variety of techniques for introducing an exogenous nucleic acid into a cell including calcium phosphate or calcium chloride precipitation, microinjection, DEAE-dextrin-mediated transfection, lipofection or electroporation.

Electroporation is carried out at approximate voltage and capacitance (and corresponding time constant) to result in entry of the DNA construct(s) into the primary or secondary cells. Electroporation can be carried out over a wide range of voltages (e.g., 50 to 2000 volts) and corresponding capacitance. Total DNA of approximately 0.1 to 500 µg is generally used.

Methods such as calcium phosphate precipitation, modified calcium phosphate precipitation and colubrine precipitation, liposome fusion and receptor-mediated gene delivery can also be used to transect cells. Primary or secondary cells can also be transfected using microinjection. A stably, transfected cell can then be isolated and cultured and sub cultivated, under culturing conditions and for sufficient time to propagate stably transfected secondary cells an produce a clonal cell strain of transfected secondary cells. Alternatively, more than one transfected cell is cultured and sub cultured, resulting in production of a heterogeneous cell strain.

Transfected primary or secondary cells undergo sufficient number doubling to produce either a clonal cell strain or a heterogeneous cell strain of sufficient size to provide the therapeutic protein to an individual in effective amounts. In general, for example, 0.1 cm$^2$ of skin is biopsies and assumed to contain 1000,000 cells; one cell is used to produce a clonal cell strain and undergoes approximately 27 doublings to produce 100 million transfected secondary cells. If a heterogeneous cell strain is to be produced from an original transfected population of approximately 1000,000 cells, only 10 doublings are needed to produce 100 million transfected cells.

The number of required cells in a transfected clonal heterogeneous cell strain is variable and depends on a variety of factors, including but not limited to, the use of the transfected cells, the functional level of the exogenous DNA is the transfected cells, the site of implantation of the transfected cells (for example, the number of cells that can be used is limited by the anatomical site of implantation), and the age, surface area, and clinical condition of the patient. The put these factors in perspective, to deliver therapeutic levels of human growth hormone in an otherwise healthy 10 kg patient with isolated growth hormone deficiency, approximately one to five hundred million transfected fibroblast would be necessary (the volume of these cells is about that of the very tip of the patient's thumb).

Implantation of Clonal Cell Strain or Heterogeneous Cell Strain of Transfected Secondary Cells The transfected cells, e.g., cells produced as described herein, can be introduced into an individual to whom the product is to be delivered. The clonal cell strain or heterogeneous cell strain is then introduced into an individual. Various routed of administration and various sites (e.g., renal sub capsular, subcutaneous, central nervous system (including intrathecal), intravascular, intrahepatic, intrasplanchnic, intraperitoneal (including intraomental), intramuscularly implantation) can be used. One implanted in individual, the transfected cells produce the product encoded by the heterologous DNA or are affected by the heterologous DNA itself. For example, an individual who has been diagnosed with diabetes, a disorder characterized by hyperglycemia, is a candidate for gene therapy cure. Hyperglycemia in diabetics is caused, in part by impaired secretion of endogenous insulin and resistance to the effects of insulin by muscle and liver tissue which results in excess glucose production in the liver.

Controlling fasting blood glucose is necessary to prevent hyperglycemic complication. GLP-1, a 37 amino acid peptide, has been found to have insulin tropic properties and delays gastric dumping to help normalize hepatic glucose production. Thus, a transfected cell which produces GLP-1 can be used to treat a subject having diabetes.

The patient has a small skin biopsy performed; this is a simple procedure which can be performed on an outpatient basis. The piece of skin, approximately the size of a match, is taken, for example, from under the arm and requires about one minute to remove. The sample is processed, resulting in isolation of the patient's cell (in case, fibroblasts) and genetically engineered to produce the GLP-1. Based on the age, weight, and clinical condition of the patient, the required number of cells are grown in large-scale culture. The entire process should require 4–6 weeks and, at the end of that time, the appropriate number of genetically engineered cells are introduced into the individual, once again as an outpatient (e.g., by injecting them back under the patient's skin). The patient is now capable of producing GLP-1 which ameliorates one or more symptoms of diabetes.

A similar approach can be used to treat other conditions or disease.

For some diseased, this will be a one-time treatment and, for others, multiple gene therapy treatments will be required.

As this example suggests, the cells used will generally be patient-specific genetically engineered cells. It is possible, however, to obtain cells from another individual of the same species or form a different species. Use of such cells might require administration of an immunosuppressant, alteration of histocompatibility antigens, or use of a barrier device to prevent rejection of the implanted cells.

Transfected primary or secondary cells can be administered alone or in conjunction with a barrier or agent for inhibiting immune response against the cell in a recipient subject. For example, an immunosuppressive agent can be administered to a subject inhibit or interfere with normal response in the subject. Preferably, the immunosuppressive agent is an immunosuppressive drug which inhibits T cell/or B cell activity in a subject. Examples of such immunosuppressive drugs commercially available (e.g., cyclosporin A is commercially avail for Sandoz Corp. East Hanover, N.J.).

An immunosuppressive agent e.g., drug, can be administered to a subject at a dosage sufficient to achieve the desired therapeutic effect (e.g., inhibition of rejection of the cells). Dosage ranges for immunosuppressive drugs are known in the art. See, e.g., Freed et al. (1992) N. Engl. J. Med. 327:1549; Spencer et al. (1992) N. Engl. J. Med. 327:1541' Widner et al. (1992) n. Engl. J. Med. 327:1556). Dosage values may vary according to factors such as the disease state, age, sex, and weight of the individual.

Another agent with can be used to inhibit T cell activity in a subject is an antibody, or fragment of derivative thereof. Antibodies capable of depleting or sequestering T cells in vivo are known in the art. Polyclonal antisera can be used, for example, anti-lymphocyte serum. Alternatively, one or more monoclonal antibodies can be used. Preferred T cell depleting antibodies include monoclonal antibodies which bind to CD2, CD3, CD4, CD8, CD40, CD40, ligand on the cell surface. Such antibodies are known in the art and are commercially available, for example, from American Type Culture Collection. A preferred antibody for binding CD3 on human T cells is OKT3 (ATCC CRL 8001).

An antibody which depletes, sequesters or inhibits T cells within a recipient subject can be administered in a dose for an appropriate time to inhibit rejection of cells upon transplantation. Antibodies are preferably administered intravenously in a pharmaceutically acceptable carrier of diluent (e.g., saline solution).

Another way of interfering with or inhibiting an immune response to the cells in a recipient subject is to use an immunobarrier. An "immunobarrier" as used herein, refers to a device which serves as a barrier between the administered cell and cells involved in immune response in a subject. For example, the cells can be administered in an implantable device. An implantable device can include the cells contained within a semi-permeable barrier, i.e., one which lets nutrients and the product diffuse in and out of the barrier but which prevents entry or larger immune system components, e.g., antibodies or complement. An implantable device typically includes a matrix, e.g., a hydrogel, or core in which cells are disposed. Optionally, a semi permeable coating can enclose the gel. If disposed within the gel core, the administered cells should be sequestered from the cells of the immune system and should be cloaked from the cells and cytotoxic antibodies of the host. Preferably, a permselective coating such as PLL or PLO is used. The coating often has a porosity which prevents components of the recipient's immune system from entering and destroying the cells within the implantable device.

Many methods for encapsulating cells are known in the art. For example, encapsulation using a water soluble gum to obtain a semi-permeable water insoluble gel to encapsulate cells for production and other methods of encapsulation are disclosed in U.S. Pat. No. 4,352,883. Other implantable devices which can be used are disclosed in U.S. Pat. No. 5,084,350, U.S. Pat. No. 5,427,935, WO 95/19743 published Jul. 27, 1995, U.S. Pat. No. 5,545,423, U.S. Pat. No. 4,409,331, U.S. Pat. No. 4,663,286, and European Patent No. 301,777.

Uses of Transfected Primary and Secondary Cells and Cell Strains

Transfected primary or secondary cells or cell strains have wide applicability as a vehicle or delivery system for therapeutic proteins.

Transfected primary or secondary cells can be used to administer therapeutic proteins (e.g., hormone, enzymes), which are presently administered intravenously, intramuscularly, or subcutaneously, which requires patient cooperation and, often medical staff participation. When transfected primary or secondary cells are used, there is no need for extensive purification of the polypeptide before it is administered to an individual, as is generally necessary with an isolated polypeptide. In addition, transfected primary or secondary cells of the present invention produce the therapeutic protein as it would normally be produced.

Preferably, the transfected cells are introduced into the omentum of a subject. Introduction of transfected cells into the omentum allows for long-term systemic delivery of a protein. The cell can be introduced into the omentum by, for example, surgical implantation, laparoscopy or direct injection, e.g., via a CT-guided needle or an ultrasound guided needle. Methods of introducing a transfected cell into the omentum are described in U.S. application Ser. No. 09/293, 665, the content of which are incorporated herein by reference.

An advantage of the use of transfected or secondary cells is that by controlling the number of cells introduced into an individual, one can control the amount of the protein delivered to the body. In addition, in some cases, it is possible to remove the transfected cells of there is no longer a need for the product. A further advantage of treatment by use of transfected primary or secondary cells of the present invention is that production of the therapeutic product can be regulated, such as through the an administration of zinc, steroids or an agent which affects transcription of a protein, product or nucleic acid product or affects the stability of a nucleic acid product.

EXAMPLES

Example I

Construction of Prepro-Somatostatin/GLP-1 Expression Plasmids

The DNA coding for human GLP-1 (7-37) was amplified from genomic DNA using the following primers:

```
                                          (SEQ ID NO:3)
IT-3: 5'-CATGCTGAAGGGACCTTTACCAGT'-3'

(SEQ ID NO:4)
IT-4: 5'-TTTCTCGAGTTATCCTCGGCCTTTCACCAGC-3'
```

The IT-4 oligo was designed to contain an XhoI site immediately downstream of the stop codon. A 105 bp PCR product was obtained and digested with XhoI. The digested product was cloned in a three-way ligation with a 300 bp PCR product containing the human growth hormone (hGH) signal peptide and pBluescript II SK+ (Stratagene). The resulting construct designated pXIT-int, was sequenced to verify that the GLP-1 sequence was correct. A 400 bp fragment from pXIT-int, containing the hGH signal peptide and GLP-1, was then used to generate the pXIT-1 expression construct.

To construct pXIT-28, amino acids through 37 and the stop codon of GLP-1 were amplified from the pXIT-1 template by PCR using Taq polymerase. The PCR was done with the following oligonucleotides:

```
                                          (SEQ ID NO:5)
oligo GC302: 5' GGAGGGACCTTTACCAGTGAT-3'

(SEQ ID NO:6)
oligo GC303: 5'-TCTCGAGTTATCCTCGGCCTT-3'
```

The fragment generated, which contained a PpuMI site at the 5' end and a XhoI site at the 3' end, was cloned into the plasmid pCR2.1-Topo (Stratagene) to generate PTA-IT4c. The fidelity of the amplified product was confirmed by sequencing PTA-IT14c.

A multibasic cleavage site (SEQ ID NO:1) and GLP-1 residues 7 through 9 were introduced immediately upstream of the GLP-1-(10-37) sequence as follows: the region of PTA-IT14c between the BamHI site in the polylinker and the PpuMI site in the GLP-1 sequence was replaced with a synthetic fragment. The sticky-ended fragment was generated by kinasing and annealing the following two oligonucleotides:

```
                                          (SEQ ID NO:7)
GC357:
5'-GATCCCGTCTCACGCGCTCGAGCTCGGAGACATGCTGAAGG-3'

(SEQ ID NO:8)
GC358:
5'-GTCCCTTCAGCATGTCTCCGAGCTCGAGCGCGTGAGACGG-3'
```

This fragment contained a BsmBI site adjacent to the 5' BamHI, and RARARR (SEQ ID NO:1) multibasic cleavage site, and amino acids 7 through 9 of GLP-1 followed by the PpuMI site (amino acid 10 starts at the PpuMI site). The resulting plasmid was designated pTA-RARARR+IT.

To facilitate metabolic labeling experiments with GLP-1 (data not shown), the valine at position 16 and the leucine at position 20 were mutated to methionines using the Quik Change mutagenesis system (Stratagene). The resulting plasmid was designated PTA-RARARR+/met. The next step was to introduce the prepro-somatostatin sequence upstream of the RARARR-GLP-1 sequence. A human prepro-somatostatin genomic clone, plasmid pgHS7-2.7, was obtained from the American Type Culture Collection (ATCC Accession Number: 65123). This was used as a template for Pfu polymerase-based overlap PCR to generate the prepro-somatostatin leader while deleting the existing intron. The 5' portion of the leader was made with the following oligonucleotides:

```
                                          (SEQ ID NO:9)
GC363: 5'-GTTGGATCCATGCTGTCCTGCCGCCTCCAGTG-3'

(SEQ ID NO:10)
GC360: 5'-GGCCAGTTCCTGCTTCCCCGCGGCAGC-3'
```

The 3' portion of the leader was made with the following oligonucleotides:

```
                                          (SEQ ID NO:11)
GC361: 5'-GGGAAGCAGGAACTGGCCAAGTACTTCTTG-3'

(SEQ ID NO:12)
GC364: 5'-CCACGTCTCTCTGCAGCTCAAGCCTCATTTCATCC-3'
```

The resulting fragments were annealed, extended with Pfu polymerase and then re-amplified with Pfu polymerase. The recombinant PCR product, contain a BamHI site at the 5' end and a BsmBI site at the 3' end, was cloned into a Stratagene vector pCR2.1 to generate pTA-PPS. The insert was sequenced.

The prepro-somatostatin leader was united with the cleavage site (SEQ ID NO:1) and GLP-1 (7-37) coding sequence as follows: pTA-RARARR+IT/met was cut with BsmBI, blunted with the Klenow fragment of DNA polymerase, then sub-cut with BamHI, treated with calf intestine alkaline phosphates (CIAP) and the 4 kb vector fragment was gel purified. The same process, without CIAP, was applied to pTA-PPS to isolate the 262 bp fragment containing the prepro-somatostatin sequence. Correct ligation of the two blunt BsmBI sites results in an in-frame union of the leader with the coding sequence for the multibasic cleavage site and GLP-1 (7-37). This was confirmed by sequencing and the plasmid was designated pre-IT28.

To facilitate the final cloning step it was necessary to eliminate an HhoI site that was contained within the coding sequence of multibasic cleavage site. The nucleotide sequence was changed without altering the corresponding amino acid sequence by Quenching mutagenesis (Stratagene).

The resulting plasmid, pre-IT28ΔXho, was digested with BamHI and HhoI and 381 bp fragment containing the prepro-somatostatin/GLP-1 fusion cassette was gel purified. Two fragments were prepared from pXAG-13, an α-galactosidase expression construct. An EcoRI/XhoI digest produced a 0.7 kb fragment that contained the human growth hormone poly A-tail. A BamHI partial digest, sub-cut with ExoRI and CIAP treated, produced a 6.5 kb fragment that contained the CMV promoter, and neomycin and β-lactamase coding regions. The three fragments were ligated, replacing the α-galactosidase coding sequence in pXAG-13 with the prepro-somatostatin/GLP-1 cassette. This construct was designated pXIT-28. For experiments that did not require metabolic labeling, the methionines at positions 16 and 20 were mutated to valine and leucine, the residues normally present in GLP-1 (Quik Change, Stratagene). This construct was designated pXIT-39.

Figure 2:
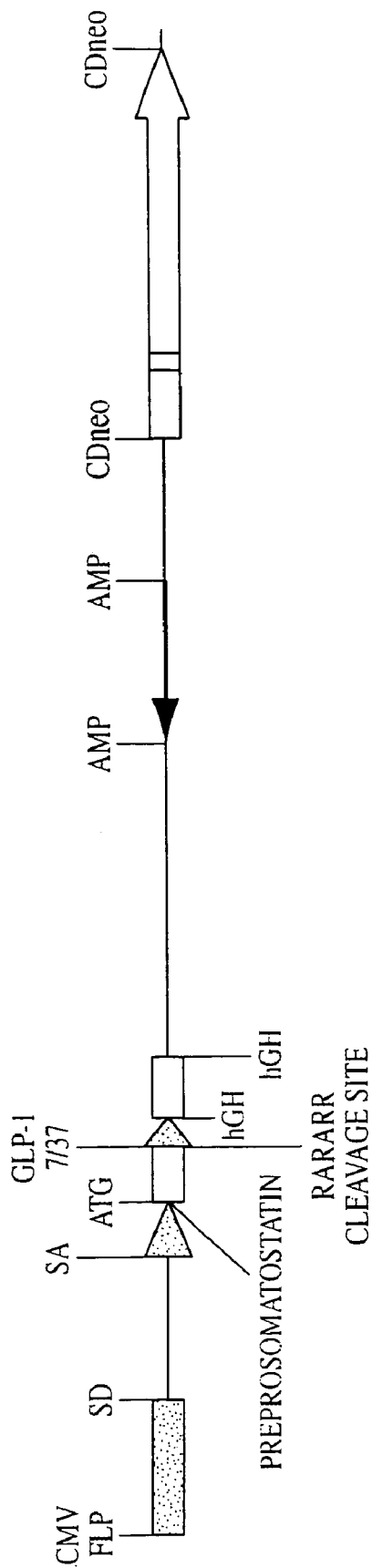
FIG. 2 depicts the pXIT-39 expression construct. The CMV promoter is shown as a bold line, interrupted by the CMV promoter intron (thin line). The prepro-somatostatin (ppSST) sequence is represented by the open box, with the translation initiation site indicated as ATG. The RARARR cleavage site (SEQ ID NO:1) and GLP-1 immediately follow ppSST and are depicted as a bold arrow. The human growth hormone polyadenylation site and coding regions for ampicillin-resistance and neomycin resistance are labeled.

The expression plasmid pXIT-39 contained the preprosomatostatin nucleotide sequence, followed by sequences for the multibasic cleavage site Arg-Ala-Arg-Ala-Arg-Arg and human GLP-1-(7-37). The construct also contained elements to allow for selection of stable, constitutive expression in human cells (FIGS. 2 and 3).

Example II

Generation of a Human Fibroblast Cell Line Expressing GLP-1

Primary culture human foreskin fibroblast (3 million) were mixed with 100 µl of conditioned media using an assay for GLP-1 (7-37) (Peninsula).

Colonies that scored positive by RIA were expanded and 5 milliliters of conditioned serum-free media was concentrated by Sep-Pak (Waters) for western blot analysis. Sep-Pak concentration was performed as follows: C-18 sep-paks (360 mg resin) were wet with 10 milliliters methanol, washed with 10 milliliters water, and equilibrated with 10 milliliters 20% acetonitrile/0.1% trifluoroacetic acid (TFA). Conditioned media was acidified to 0.2% TFA and passed through the Sep-Pak two times. The column was washed with 10 milliliters of 80% acentonitrile/0.1% TFA. The elute was frozen and lyophilized.

For western blot, the elute was solubilized in tricine sample buffer (200 mM 16% resolving gel using a tricine buffer system. Peptides were blotted to PVDF membranes in 10 mM CAPS with 40% methanol. A polyclonal antibody to GLP-1, TK3 1, was used to detect pro-somatostatin/GLP-1 and mature GLP-1, Primary human fibroblast cells were transfected with pXIT-39 plasmid DNA. G418-resistant clones were selected and screened for the ability to secrete GLP-1 by radioimmunoassay and western blot analysis of 24 hour conditioned media. Several clones were found to secrete a peptide that corresponded to GLP-1 by molecular weight and immunoreactivity to anti-GLP-1 antis era. One clone, FG39-38, was selected for further analysis.

Western blot of conditioned media from the human fibroblast cell line FG39-38 showed and upper band corresponds to the fusion protein and the lower band to processed GLP-1.

Example III

Purification and Amino Acid Sequencing of Human Fibroblast Produced GLP-1

Based on RIA and western blot data, one clone, FG39-38, was chosen to use as a source of human fibroblast-derived GLP-1 (HF-GLP-1). FG39-38 cells were cultured in DMEM with 10% BCS until confluent in T-75 flasks. Media was removed and replaced with 10 milliliters serum-free DMEM. After 24 hours conditioned media was collected and stored at −20° C.

A 20 cc Sep-Pak (Waters) containing 5 grams of C-18 resin was wet with 20 milliliters methanol, washed with 20 milliliters water, and equilibrated with 40 milliliters 20% acentronitirle/0.1% TFA. Ninety milliliters of FG39-38 conditioned media was acidified to 0.2% TFA (final concentration and passed through the Sep-Pak two times). The column was washed with 50 milliliters of 20% acetonitrile/0.1% TFA and then eluted with four 10 ml aliquots of 80% acetonitrile/0.1% TFA. The four elute aliquots were frozen and lyophilized.

Lyophilized peptides were solubilized in tricine sample buffer and separated by polyacrylamide gel electroporesis with 4% stack and 16% resolving gel using a tricine buffer system. The peptides were then blotted to PVDF membranes and visualized by stain with Coomassie blue. A low molecular weight band that co-migrated with GLP-1 immunoreactive band from a western blot that was run in parallel was excised and submitted for N-terminal sequence analysis.

The sequence was found to be identical to human GLP-1 (7-36) as shown in FIG. 4, FIG. 4 shows the alignment of human GLP-1 (7-37), human GLP-1 (7-36), and GLP-1 derived from the human fibroblast cell line FG39-38 (HF GLP-1). Sequence identity between human GLP-1 (7-36) and human fibroblast GLP-1 is 100%. The Arg 30 of human GLP-1 (7-36) is amidated. The micro sequencer used to sequence human fibroblast GLP-1 did not distinguish normal Arg from amidated Arg. The presence or absence of an amide group will be determined by mass spectrometry. No residue was detected after Arg 30 of HF GLP-1 in this sample. However, radioimmunoassay data indicates that both the 7-37 and 7-36 peptides are secreted by human fibroblasts transfected with pXIT-39.

Example IV

Gene Therapy with Human Fibroblast Cell Lines Expressing GLP-1

Figure 5:
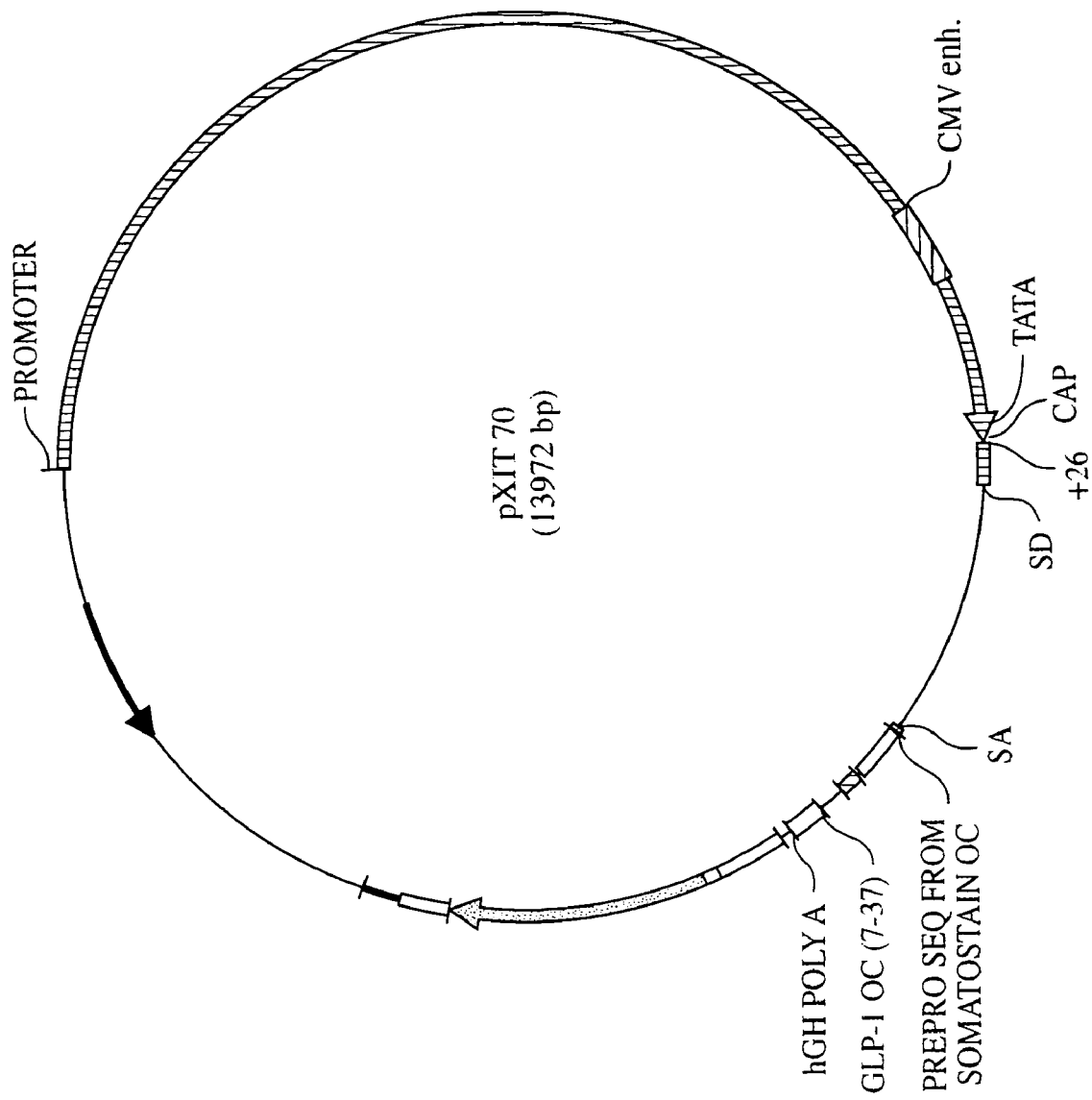
FIG. 5 depicts the pXIT-70 expression construct. The promoter is shown as bold arrow. The CMV enhancer is shown as a hatched box. The prepro-somatostatin sequence is labeled and represented by the open box. This region has been modified by codon optimization (OC). GLP-1 immediately follows the prepro sequence and is depicted as a black box. The GLP-1 has also been modified by codon optimization (OC). The human growth hormone polyadenylation site is labeled.
Figure 6:
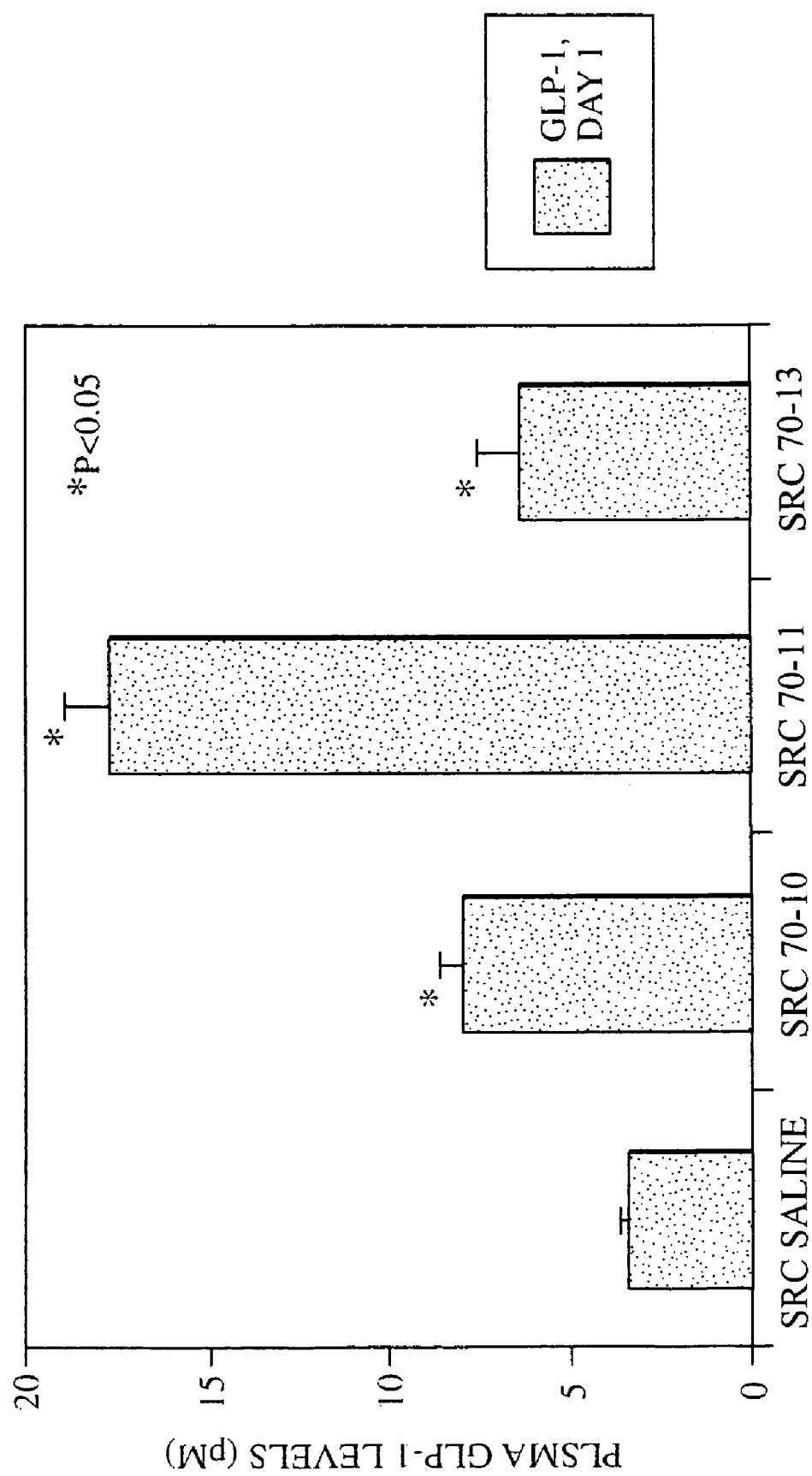
FIG. 6 is a graph showing GLP-1 levels in plasma samples of nude mice receiving subrenal capsule injection of human fibroblasts clones expressing prepro-somatostatin/GLP-1 fusion peptides. The graph depicts plasma levels of GLP-1 in mice receiving an injection of human fibroblasts clones FG 70-10 ("src 70-10"), FG 70-11 ("src 70-11"), or FG 70-13 ("src 70-30") or a saline control ("src saline").

Three human fibroblast clones expressing GLP-1 (FG70-10, FG70-11 and FG70-13) were expanded for implantation. See FIG. 5 which depicts the pXIT-70 construct used to prepare the human fibroblast clones expressing GLP-1. Each clone was implanted into the subrenal capsule of ten female nude mice, with each mouse receiving three million cells. Control mice received a subrenal capsule injection of saline. Twenty-four hours after implantation, mice were anesthetized with isofluorane and blood was collected from the retro-orbital sinus. Plasma GLP-1 levels were measured using ELISA (Linco) specific for active GLP-1 (i.e., GLP-1-(7-37) and GLP-1-(7-36) amide)). As shown in FIG. 6, GLP-1 plasma levels were increased up to 500% over basal levels twenty-four hours after implantation.

Implantation of human fibroblasts expressing proSST/GLP-1 results in a significant increase in plasma GLP-1 levels in nude mice.

Example V

Accumulation and Secretion of GLP-1 peptides and Pro-Somatostatin/GLP-1 Peptides Primary human fibroblasts (HF) were transfected with the proSST/GLP-1 expression construct pXIT-28. In this construct, two methionine residues have been introduced into the GLP-1 sequence to facilitate metabolic labeling experiments. The proSST sequence contains one methionine. G418-resistant clones were incubated in serum-free media containing 100 uCi/ml [$^{35}$S]-methionine for 24 hours. GLP peptides were then immunoprecipitated from conditioned media with the polyclonal anti-GLP-1 antisera, TK31, separated by gel electroporesis and visualized by autoradiography. Several clones secreted proSST/GLP-1 and GLP-1 into the culture media. Roughly equal amounts of precursor and product are found in conditioned media from these clones after the 24 hour labeling period. Clone 28-17 was chosen for further study.

The ratio of precursor to product immediately after secretion from human fibroblasts was determined by pulse-chase experiments. Clone 28-17 was exposed to a "pulse" of 1000 uCi/ml [$^{35}$S]-methionine for 10 minutes, followed by a "chase" of media containing excess cold methionine. Lysate and conditioned media were collected at 0, 10, 20, 40, 60 and 120 minutes after removal of [$^{35}$S]-methionine, and GLP peptides were visualized as described above. Precursor and product are clearly visible in the media 2 hours after the pulse. The amount of proSST/GLP-1 present at this time is much less than the amount of GLP-1, despite the fact that the 3:2 ratio of [$^{35}$S]-methionine in the precursor versus the product would favor detection of proSST/GLP-1.

Figure 7:
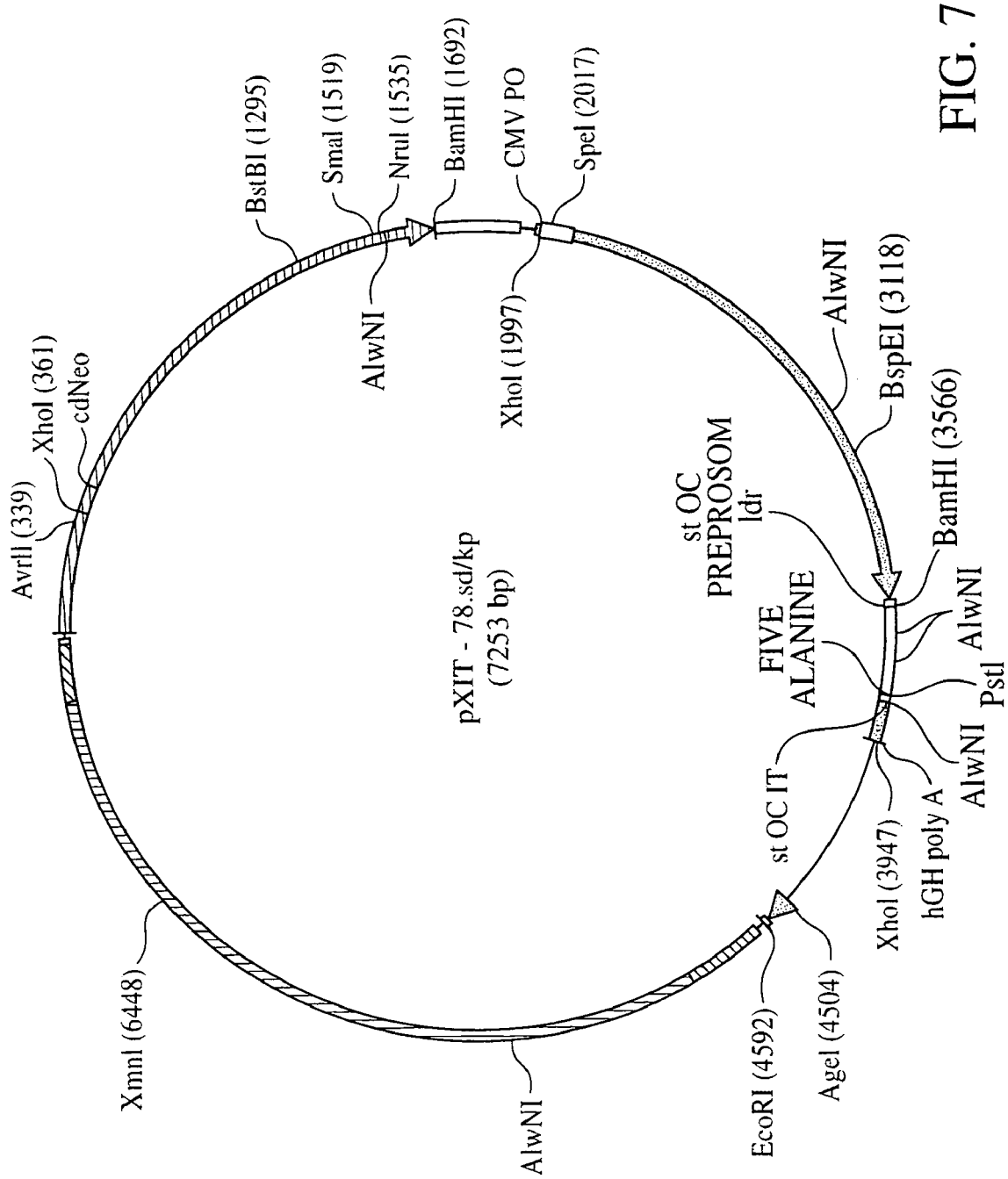
FIG. 7 depicts the pXIT-78 expression construct. The CMV promoter is shown as a bold gray arrow. The prepro-somatostatin (ppSST) sequence is represented by the open box. The modified cleavage site having five alanine residues is labeled as "five alanine" and depicted by a gray box. The GLP-1 sequence immediately follows the alanine residues and is depicted as a dark gray box. The human growth hormone polyadenylation site and coding regions for neomycin resistance are labeled.

The pulse-chase experiment indicates that human fibroblasts stably transfected with pXIT-28 secrete much more mature GLP-1 than proSST/GLP-1 precursor. However, after steady-state labeling for 24 hours, the conditioned media from human fibroblasts contain equivalent amounts or precursor and product. This data suggests that proSST/GLP-1 accumulates because it is more stable in conditioned media than GLP-1, and that the SST proregion of the precursor may protect GLP-1 from degradation. The enhanced stability of the precursor has important biological consequences. In vivo, proSST/GLP-1 may bind directly to GLP-1 receptors, and therefore function as a GLP-1 analogue with increased half-life. The longest half-life may be achieved by a proSST/GLP-1 fusion protein that cannot be processed to mature GLP-1, thereby preventing degradation of the peptide. Such a construct has been generated by replacing the arginines in the cleavage site with alanines. See FIG. 7.

All patents and references cited herein are incorporated in their entirety by reference. Other embodiments are within the following claims.

What is claimed is:

1. A nucleic acid construct for expression of a glucagon-like peptide-1 (GLP-1) or a variant thereof, comprising:
   a nucleic acid sequence encoding a signal peptide from the pre-region of somatostatin;
   a nucleic acid sequence encoding the pro-region of a somatostatin, or a functional fragment or a variant of the pro-region of a somatostatin wherein the functional fragment or variant differs from the wild-type amino acid sequence by at least 1 but not more than 5 amino acid residues and is sufficient to promote secretion from a non-endocrine cell; and
   a nucleic acid sequence encoding a GLP-1 or a variant thereof.

2. The construct of claim 1, wherein the nucleic acid sequence encoding the signal peptide comprises the pre-region of a somatostatin.

3. The construct of claim 1, wherein the construct further comprises a nucleotide sequence encoding a cleavage site between the sequence encoding the pro-region or functional fragment or variant thereof and the sequence encoding the GLP-1 or a variant thereof.

4. The construct of claim 3, wherein the cleavage site is a multibasic, dibasic or monobasic cleavage site.

5. The construct of claim 3, wherein the cleavage site is an endoprotease cleavage site.

6. The construct of claim 5, wherein the cleavage site is recognized by a pro-protein convertase.

7. The construct of claim 6, wherein the pro-protein convertase is furin, substilisin-related pro-protein convertase, PC1, PC2, PC6 or PC7.

8. The construct of claim 1, further comprising at least one regulatory sequence.

9. The construct of claim 1, wherein the variant is selected from the group consisting of: GLP-1 (7-34), GLP-1 (7-35), GLP-1 (7-36), GLP-1 (7-37), Gln$^9$-GLP-1 (7-37), Thr$^{16}$-Lys$^{18}$-GLP-1 (7-37), Lys$^{18}$-GLP-1 (7-37), Gly$^8$-GLP-1, Met$^{16}$-Met$^{20}$-GLP-1 (7-37).

10. A method of making a cell capable of secreting a GLP-1 or a variant thereof, comprising:
providing a non-endocrine cell; and
introducing into the cell a nucleic acid construct of claim 1 or 3 to thereby obtain a cell capable of expressing the GLP-1 or variant thereof.

11. The method of claim 10, wherein the cell is a primary cell.

12. The method of claim 10, wherein the cell is a secondary cell.

13. The method of claim 10, wherein the cell is a mammalian cell.

14. The method of claim 10, wherein the sequence encoding the signal peptide comprises the pre-region of a somatostatin.

15. A nucleic acid construct for expression of GLP-1, comprising: a nucleic acid sequence encoding a fusion protein comprising a signal peptide from the pre-region of somatostatin; the pro-region of a somatostatin; and GLP-1.

16. A nucleic acid construct for expression of GLP-1 comprising: a nucleic acid sequence encoding a fusion protein comprising the prepro-region of somatostatin and GLP-1.

17. An isolated non-endocrine cell comprising a nucleic acid sequence that encodes a fusion protein that comprises (a) a signal peptide from the pre-region of somatostatin, (b) a pro-region of a somatostatin or a functional fragment or a variant of the pro-region of a somatostatin wherein the functional fragment or variant differs from the wild-type amino acid sequence by at least 1 but not more than 5 amino acid residues and is sufficient to promote secretion from a non-endocrine cell, and (c) a glucagon-like peptide-1 (GLP-1) or a variant thereof, the cell being capable of secreting the GLP-1 or variant thereof.

18. The cell of claim 17, wherein the encoded fusion protein further comprises a cleavage site between the pro-region or functional fragment or variant thereof and the GLP-1 or variant thereof.

19. The cell of claim 18, wherein the cleavage site is a multibasic, dibasic or monobasic cleavage site.

20. The cell of claim 18, wherein the cleavage site is an endoprotease cleavage site.

21. The cell of claim 20, wherein the cleavage site is recognized by a pro-protein convertase.

22. The cell of claim 21, wherein the pro-protein convertase is furin, PACE4, substilisin-related pro-protein convertase, PC1, PC2, PC6 or PC7.

23. The cell of claim 18, wherein the cleavage site is a blood coagulation factor cleavage site.

24. The cell of claim 17, wherein the cell is capable of expressing the GLP-1 or variant thereof in mature form without the signal peptide and pro-region of somatostatin or functional fragment or variant thereof.

25. The cell of claim 17, wherein the cell is a primary cell.

26. The cell of claim 17, wherein the cell is a secondary cell.

27. The cell of claim 17, wherein the cell is a mammalian cell.

28. The cell of claim 27, wherein the cell is a human cell.

29. The cell of claim 27, wherein the cell is a fibroblast or a myoblast.

30. The cell of claim 17, wherein the cell is one in which somatostatin is not normally expressed.

31. The cell of claim 17, wherein the nucleic acid sequence that encodes the fusion protein is operably linked to at least one regulatory sequence sufficient for expression of the fusion protein in the cell.

32. A method of making a GLP-1 or a variant thereof comprising culturing the cell of claim 17 to thereby obtain GLP-1 or a variant thereof.

33. The method of claim 32, wherein the GLP-1 or variant thereof is obtained in mature form without the signal peptide and pro-region of somatostatin or functional fragment or variant thereof.

34. The method of claim 32, wherein the GLP-1 or variant thereof is obtained as part of a fusion peptide which further comprises the pro-region of somatostatin or the functional fragment or variant thereof.

35. The cell of claim 17, wherein the variant is selected from the group consisting of: GLP-1 (7-34), GLP-1 (7-35), GLP-1 (7-36), GLP-1 (7-37), Gln$^9$-GLP-1 (7-37), Thr$^{16}$-Lys$^{18}$-GLP-1 (7-37), Lys$^{18}$-GLP-1 (7-37), Gly$^8$-GLP-1, Met$^{16}$-Met$^{20}$-GLP-1 (7-37).

36. An isolated non-endocrine, mammalian cell comprising a nucleic acid sequence encoding a fusion protein comprising: a signal peptide from the pre-region of somatostatin, the pro-region of somatostatin, and a GLP-1, wherein the cell secretes the GLP-1.

37. The cell of claim 36, wherein the cell is a human cell.

38. The cell of claim 36, wherein the cell is a fibroblast.

39. An isolated non-endocrine, human cell comprising a nucleic acid sequence encoding a fusion protein comprising: the prepro-region of somatostatin and GLP-1, wherein the cell secretes GLP-1.

40. An isolated fibroblast comprising a nucleic acid sequence encoding a fusion protein comprising: the prepro-region of somatostatin and GLP-1 or a variant thereof, wherein the variant is selected from the group consisting of: GLP-1 (7-34), GLP-1 (7-35), GLP-1 (7-36), GLP-1 (7-37), Gln$^9$-GLP-1 (7-37), Thr$^{16}$-Lys$^{18}$-GLP-1 (7-37), Lys$^{18}$-GLP-1 (7-37), Gly$^8$-GLP-1, Met$^{16}$-Met$^{20}$-GLP-1 (7-37), and the cell secretes the GLP-1 or variant thereof.

41. A method of making GLP-1 or a variant thereof comprising culturing the fibroblast of claim 40 to thereby obtain the GLP-1 or variant thereof.

* * * * *

SEQUENCE LISTING

```
<160> NUMBER OF SEQ ID NOS: 14

<210> SEQ ID NO 1
<211> LENGTH: 6
<212> TYPE: PRT
<213> ORGANISM: Artificial Sequence
<220> FEATURE:
<223> OTHER INFORMATION: multibasic cleavage site

<400> SEQUENCE: 1

Arg Ala Arg Ala Arg Arg
 1               5

<210> SEQ ID NO 2
<211> LENGTH: 396
<212> TYPE: DNA
<213> ORGANISM: Artificial Sequence
<220> FEATURE:
<223> OTHER INFORMATION: Synthetically generated oligonucleotide

<400> SEQUENCE: 2
ggatccatgc tgtcctgccg cctccagtgc gcgctggctg cgctgtccat cgtcctggcc      60
ctgggctgtg tcaccggcgc tccctcggac cccagactcc gtcagtttct gcagaagtcc     120
ctggctgctg ccgcggggaa gcaggaactg gccaagtact tcttggcaga gctgctgtct     180
gaacccaacc agacggagaa tgatgccctg gaacctgaag atctgtccca ggctgctgag     240
caggatgaaa tgaggcttga gctgcagcgc gcacgagctc ggagacatgc tgaagggacc     300
tttaccagtg atgtaagttc ttatttggaa ggccaagctg ccaaggaatt cattgcttgg     360
ctggtgaaag gccgaggata actcgagtaa ctcgag                               396

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
catgctgaag ggacctttac cagt                                             24

<210> SEQ ID NO 4
<211> LENGTH: 31
<212> TYPE: DNA
```

```
<213> ORGANISM: Artificial Sequence
<220> FEATURE:
<223> OTHER INFORMATION: primer

<400> SEQUENCE: 4
tttctcgagt tatcctcggc ctttcaccag c                                    31

<210> SEQ ID NO 5
<211> LENGTH: 21
<212> TYPE: DNA
<213> ORGANISM: Artificial Sequence
<220> FEATURE:
<223> OTHER INFORMATION: oligonucleotide for PCR

<400> SEQUENCE: 5
ggagggacct ttaccagtga t                                               21

<210> SEQ ID NO 6
<211> LENGTH: 21
<212> TYPE: DNA
<213> ORGANISM: Artificial Sequence
<220> FEATURE:
<223> OTHER INFORMATION: oligonucleotide for PCR

<400> SEQUENCE: 6
tctcgagtta tcctcggcct t                                               21

<210> SEQ ID NO 7
<211> LENGTH: 41
<212> TYPE: DNA
<213> ORGANISM: Artificial Sequence
<220> FEATURE:
<223> OTHER INFORMATION: oligonucleotide for PCR

<400> SEQUENCE: 7
gatcccgtct cacgcgctcg agctcggaga catgctgaag g                         41

<210> SEQ ID NO 8
<211> LENGTH: 40
<212> TYPE: DNA
<213> ORGANISM: Artificial Sequence
<220> FEATURE:
<223> OTHER INFORMATION: oligonucleotide for PCR

<400> SEQUENCE: 8
gtcccttcag catgtctccg agctcgagcg cgtgagacgg                           40

<210> SEQ ID NO 9
<211> LENGTH: 32
<212> TYPE: DNA
<213> ORGANISM: Artificial Sequence
<220> FEATURE:
<223> OTHER INFORMATION: oligonucleotide for PCR

<400> SEQUENCE: 9
gttggatcca tgctgtcctg ccgcctccag tg                                   32

<210> SEQ ID NO 10
<211> LENGTH: 27
<212> TYPE: DNA
<213> ORGANISM: Artificial Sequence
<220> FEATURE:
<223> OTHER INFORMATION: oligonucleotide for PCR

<400> SEQUENCE: 10
ggccagttcc tgcttccccg cggcagc                                         27
```

```
<210> SEQ ID NO 11
<211> LENGTH: 30
<212> TYPE: DNA
<213> ORGANISM: Artificial Sequence
<220> FEATURE:
<223> OTHER INFORMATION: oligonucleotide for PCR

<400> SEQUENCE: 11
gggaagcagg aactggccaa gtacttcttg                                          30

<210> SEQ ID NO 12
<211> LENGTH: 35
<212> TYPE: DNA
<213> ORGANISM: Artificial Sequence
<220> FEATURE:
<223> OTHER INFORMATION: oligonucleotide for PCR

<400> SEQUENCE: 12
ccacgtctct ctgcagctca agcctcattt catcc                                    35

<210> SEQ ID NO 13
<211> LENGTH: 31
<212> TYPE: PRT
<213> ORGANISM: Homo sapiens

<400> SEQUENCE: 13

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
             20                  25                  30

<210> SEQ ID NO 14
<211> LENGTH: 30
<212> TYPE: PRT
<213> ORGANISM: Artificial Sequence
<220> FEATURE:
<223> OTHER INFORMATION: synthetically generated polypeptide

<400> SEQUENCE: 14

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
             20                  25                  30
```